United States Patent [19]

Anderson et al.

[11] 4,399,141

[45] Aug. 16, 1983

[54] 5-ALKYL OR HYDROXYALKYL SUBSTITUTED-10,11-DIHYDRO-5H-DIBENZO[a/d]CYCLOHEPTEN-5,10-IMINES AND ANTICONVULSANT USE THEREOF

[75] Inventors: Paul Anderson, Lansdale; Marcia E. Christy, Perkasie; Ben E. Evans, Lansdale, all of Pa.

[73] Assignee: Merck & Co., Inc., Rahway, N.J.

[21] Appl. No.: 272,864

[22] Filed: Jun. 12, 1981

Related U.S. Application Data

[63] Continuation-in-part of Ser. No. 74,367, Sep. 10, 1979, abandoned, which is a continuation-in-part of Ser. No. 912,772, Jun. 5, 1978, abandoned, which is a continuation-in-part of Ser. No. 834,639, Sep. 19, 1977, abandoned.

[51] Int. Cl.³ .................. A61K 31/435; C07D 455/00
[52] U.S. Cl. .................................. 424/256; 546/72; 546/204; 568/325; 564/308
[58] Field of Search .......................... 546/72; 424/256

[56] References Cited

U.S. PATENT DOCUMENTS

| 3,892,756 | 7/1975 | Nedelec et al. | 260/289 C |
| 4,052,508 | 10/1977 | Anderson et al. | 424/258 |
| 4,064,139 | 12/1977 | Anderson et al. | 260/313.1 |
| 4,123,546 | 10/1978 | Haire | 424/274 |

OTHER PUBLICATIONS

Clineschmidt et al., Drug Devel. Res., 2:123–134, 147–163 (1982).

*Primary Examiner*—Donald G. Daus
*Assistant Examiner*—D. B. Springer
*Attorney, Agent, or Firm*—William H. Nicholson; Mario A. Monaco

[57] ABSTRACT

5-Substituted-10,11-dihydro-5H-dibenzo[a,d]cyclohepten-5,10-imines, derivatives and pharmaceutically acceptable salts thereof are useful as anticonvulsants.

18 Claims, No Drawings

5-ALKYL OR HYDROXYALKYL SUBSTITUTED-10,11-DIHYDRO-5H-DIBENZO[a,d]CYCLOHEPTEN-5,10-IMINES AND ANTICONVULSANT USE THEREOF

BACKGROUND OF THE INVENTION

This is a continuation-in-part of copending application Ser. No. 74,367, filed Sept. 10, 1979 abandoned which in turn is a continuation-in-part of Ser. No. 912,772, filed June 5, 1978, (now abandoned) which in turn is a continuation-in-part of application, Ser. No. 834,639, filed Sept. 19, 1977, also abandoned.

This invention is concerned with novel 5-substituted-10,11-dihydro-5H-dibenzo[a,d]cyclohepten-5,10-imines, derivatives, optical isomers and pharmaceutically acceptable salts thereof which are useful as anticonvulsants.

Structurally related compounds are known in the art to have some of the same utilities. For example U.S. Pat. No. 3,892,756 discloses 10,11-dihydro-5H-dibenzo[a,d]cyclohepten-5,10-imine and derivatives which are unsubstituted at the 5-bridgehead carbon; and Belgian Pat. No. 829,075 discloses 9,10-dihydroanthracen-9,10-imines and derivatives.

It is an object of this invention to provide the novel compounds, 5-substituted-10,11-dihydro-5H-dibenzo[a,d]cyclohepten-5,10-imines, which are surprisingly more active than the unsubstituted analogs; novel processes for their synthesis; pharmaceutical compositions comprising them as active ingredient; and a novel method of treatment where there is an indicated need for an anticonvulsant.

DETAILED DESCRIPTION OF THE INVENTION

The novel compounds of this invention have structural formula:

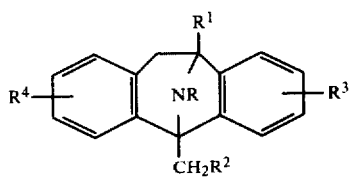

or a pharmaceutically acceptable salt thereof, wherein R is
(1) hydrogen
(2) lower alkyl, especially $C_{1-5}$ alkyl, preferably methyl or ethyl,
(3) lower alkenyl, especially $C_{2-5}$ alkenyl, preferably vinyl or allyl,
(4) phenyl (or substituted phenyl)-lower alkyl, especially phenyl (or substituted phenyl)-$C_{1-3}$ alkyl, preferably benzyl or substituted benzyl, wherein the substituent is halo such as fluoro, chloro or bromo,
(5) lower cycloalkyl, especially $C_{3-6}$ cycloalkyl, preferably cyclopropyl or cyclohexyl,
(6) lower(cycloalkyl-alkyl), especially $C_{3-6}$ cycloalkyl-$C_{1-3}$ alkyl,
(7) di(lower alkyl)amino-lower alkyl, preferably di($C_{1-3}$ alkyl)amino-$C_{1-3}$ alkyl, especially dimethylaminoethyl; or
(8) hydroxy;

$R^1$ is
(1) hydrogen,
(2) lower alkyl, especially $C_{1-5}$ alkyl, preferably methyl or ethyl,
(3) lower alkenyl, especially $C_{2-5}$ alkenyl, preferably vinyl or allyl,
(4) phenyl-lower alkyl, especially phenyl-$C_{1-3}$ alkyl, preferably benzyl,
(5) lower cycloalkyl, especially $C_{3-6}$ cycloalkyl, preferably cyclopropyl or cyclohexyl, or
(6) lower(cycloalkyl-alkyl), especially $C_{3-6}$ cycloalkyl-$C_{1-3}$ alkyl, —$CH_2R^2$ is
(1) loweralkyl, especially $C_{1-5}$ alkyl, preferably methyl or ethyl,
(2) lower alkenyl, especially $C_{2-5}$ alkenyl, preferably vinyl or allyl,
(3) phenyl-lower alkyl, especially phenyl-$C_{1-3}$ alkyl, preferably benzyl.
(4) lower(cycloalkyl-alkyl), especially $C_{3-6}$ cycloalkyl-$C_{1-3}$ alkyl, preferably cyclopropylmethyl,
(5) di(lower alkyl)amino-lower alkyl, especially di($C_{1-3}$ alkyl)amino-$C_{1-3}$ alkyl, preferably dimethylaminopropyl; or
(6) hydroxy-lower alkyl, especially hydroxy-$C_{2-3}$ alkyl, preferably hydroxyethyl; and $R^3$ and $R^4$ are independently,
(1) hydrogen,
(2) halogen, such as chloro, bromo, fluoro, or iodo,
(3) lower alkoxy, especially $C_{1-5}$ alkoxy, preferably methoxy,
(4) trifluoromethylthio,
(5) cyano,
(6) carboxy, or
(7) hydroxy.

A preferred group of compounds is that wherein $R^1$ is hydrogen.

Another preferred group of compounds is that wherein $R^1$, $R^3$ and $R^4$ are hydrogen.

Where $R^3$ and/or $R^4$ are other than hydrogen, it is preferred that they occupy the 2, 3, 7 or 8 positions of the tricyclic ring system.

A preferred definition for —$CH_2R^2$ is $C_{1-5}$ alkyl, especially methyl or ethyl, preferably methyl.

Preferred definitions for R are hydrogen, $C_{1-5}$ alkyl, such as methyl, ethyl or propyl, $C_{2-5}$ alkenyl, such as allyl and $C_{3-6}$ cycloalkyl-$C_{1-3}$ alkyl such as cyclopropylmethyl.

The novel compounds of this invention wherein R is hydrogen are generally prepared by reduction of the N-hydroxy analog. The preferred reducing agent is nascent hydrogen generated by the action of a metal, preferably zinc with an acid such as acetic acid at 40° to 100° C. for 1 to about 10 hours.

The novel compounds are also prepared by ring closure of a 10-NHR-5-(=$CHR^2$)-10,11-dihydro-5H-dibenzo[a,d]cycloheptene by treatment with a strong base such as an organometallic reagent, for example, n-butyllithium in an ethereal solvent, such as tetrahydrofuran, 1,2-dimethoxyethane or the like at about 0° C. to about 30° C. for about 5 minutes to about 1 hour.

Where —$CH_2R^2$ is hydroxy-lower alkyl, the final step in its synthesis is reduction of the lower alkoxy-carbonyl precursor. The preferred reducing agent is lithium aluminum hydride in an ethereal solvent such as diethyl ether, tetrahydrofuran, 1,2-dimethoxyethane, or the like at a temperature of about 15° C. to about 100° C.

until the reduction is substantially complete in about 1 to about 6 hours. This procedure also serves to hydrogenolyze a bridgehead halo group employed in the exemplified synthetic scheme.

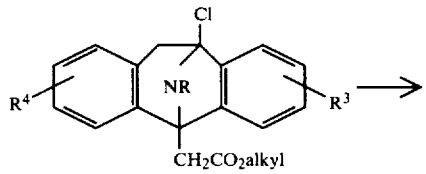

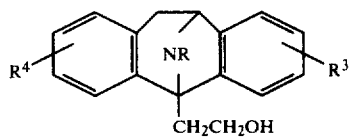

Where R is other than hydrogen, the novel compounds are prepared by alkylation of the compounds wherein R is hydrogen with the appropriate reagent of formula R-halo wherein halo represents chloro, bromo or iodo. The reaction is normally conducted in an inert solvent such a benzene, or toluene. However, the alkylating reagent, depending on its physical properties, may be used in sufficiently excess amount to act as solvent. It is preferred to conduct the reaction in the presence of an acid acceptor such as an inorganic carbonate such as sodium carbonate, an organic base such as pyridine, or a basic resin. Temperatures of about 50° C. to about 100° C. may be employed over reaction times of about 10 hours to about 5 days.

Where R is alkyl or substituted alkyl, the compounds also may be prepared by reduction of an N-acyl compound such as alkoxycarbonyl to give methyl or other alkanoyl groups to provide the other alkyl groups. The preferred reducing system is a metal hydride such as lithium aluminum hydride or borane in an ethereal solvent such as ether, tetrahydrofuran or 1,2-dimethoxyethane or the like. The reaction proceeds satisfactorily at room temperature but temperatures from about 0° C. to about 50° C. are appropriate with reaction times of 1-13 hours.

Novel compounds having substituents on the benzenoid rings are generally prepared by metathesis of the appropriate bromo or iodo compound. For example treatment with a sodium lower alkoxide in the presence of copper dust in an inert organic solvent such as dimethylformamide at 50°-150° C. for 1-10 hours yields the corresponding lower alkoxy compound.

Alternatively, if $R^3$ or $R^4$ is a relatively stable substituent such as lower alkoxy, the starting material, 5H-dibenzo[a,d]cyclohepten-5-one can be prepared with $R^3$ or $R^4$ in place by the well-known benzalphthalide route described by Cope et al., J. Amer. Chem. Soc., 73, 1673 (1951) followed by synthesis of the desired 5,10-imine.

The 2-, 3-, 7- or 8-hydroxy compounds are prepared from the corresponding alkoxy, preferably methoxy, compounds by de-etherification. The preferred process comprises heating with pyridine hydrochloride at 200°-220° C. for 3-10 hours.

Treatment of a bromo or iodo compound with cuprous cyanide in an inert organic solvent such as dimethylformamide at reflux temperature for 1-10 hours yields the corresponding cyano compound.

Hydrolysis of the above cyano compounds with a mineral acid such as hydrochloric acid at about 50° to 150° C. and especially at reflux temperature produces the corresponding carboxy substituted compounds.

Also treatment of the bromo or iodo compounds with bis(trifluoromethylthio)mercury and copper dust in an inert organic solvent such as dimethylformamide or quinoline at about 100°-200° C. for 1-10 hours yields the trifluoromethylthio derivatives.

The novel compounds can be resolved into their optical isomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base.

The starting materials and processes used for preparing the intermediates used in the above described processes are fully described in the Examples.

Also included within the scope of the present invention are the non-toxic pharmaceutically acceptable salts of the novel compounds. Acid addition salts of the imine compounds are formed by mixing a solution of the imine with a solution of a pharmaceutically acceptable non-toxic acid such as hydrochloric acid, fumaric acid, maleic acid, succinic acid, acetic acid, citric acid, tartaric acid, phosphoric acid, or the like. Where the novel compound carries a carboxylic acid group, the invention also contemplates sodium, potassium, and calcium salts thereof.

In the method of treatment aspect of the present invention, the novel imines of this invention are useful as anticonvulsants at a dosage level of from about 0.01 to about 20 mg. per kilogram of body weight preferably about 0.05-2 mg/kg of body weight on a regimen of 1-4 times a day. It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a member of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The following Examples representatively illustrate, but do not limit, the product, process, method of treatment, or compositional aspects of the present invention.

EXAMPLE 1

5-Methyl-10-11-dihydro-5H-dibenzo[a,d]cyclohepten-5,10-imine and oxalate salt

Step A: Preparation of 10-(1-piperidyl)-5H-dibenzo[a,d]cyclohepten-5-one

A mixture of 71.3 g of 10-bromo-5H-dibenzo[a,d]cyclohepten-5-one, 50 ml. of piperidine, 1 liter of t-butanol and finally 33.6 g of potassium t-butoxide was stirred under reflux 2 hours, then at room temperature overnight. The mixture was filtered, and concentrated to dryness. The residue was slurried with water and decanted. The residue was slurried with methanol and filtered to give 59.8 g of 10-(1-piperidyl)-5H-dibenzo[a,d]cyclohepten-5-one, m.p. 103°–105° C.

Step B: Preparation of 5-hydroxy-5-methyl-10-(1-piperidyl)-5H-dibenzo[a,d]cycloheptene A solution of 140 ml. of 1.8 molar methyl lithium in ether and 250 ml. of ether at 5°–10° C. under nitrogen was treated dropwise with a solution of 59 g of 10-(1-piperidyl)-5H-dibenzo[a,d]cyclohepten-5-one in 250 ml of tetrahydrofuran. After a total of 2 hours, the mixture was poured onto ice and allowed to stand until the ice melted. The mixture was extracted well with ether and the extract was dried (Na$_2$SO$_4$), filtered, and concentrated to dryness, the residue being used directly in the next step.

Step C: Preparation of 5-methylene-10-oxo-10,11-dihydro-5H-dibenzo[a,d]cycloheptene The carbinol from Step B was dissolved in 500 ml of 10N ethanolic hydrogen chloride and 30 ml concentrated hydrochloric acid and heated under reflux overnight. The solvent was evaporated and the residue was extracted with 500 ml of benzene. The extract was dried and concentrated to dryness. The residue was extracted with 300 ml of boiling hexane. On cooling the extract deposited 18.5 g solid which after recrystallization from hexane gave 16.5 g of 5-methylene-10-oxo-10,11-dihydro-5H-dibenzo[a,d]cycloheptene, m.p. 84°–86° C.

Step D: Preparation of 10-hydroximino-5-methylene-10,11-dihydro-5H-dibenzo[a,d]cycloheptene A mixture of 16.5 g of the oxo-compound from Step C, 6.6 g of hydroxylamine hydrochloride, 8.2 of sodium acetate and 300 ml of methanol was heated under reflux for 5 hours. The solvent was evaporated and the residue was treated with 250 ml of water. The mixture was extracted with 3×150 ml of ether, and the extract was dried, filtered, and evaporated to give 16.8 g of 10-hydroxyimino-5-methylene-10,11-dihydro-5H-dibenzo[a,d]cycloheptene, m.p. 156°–160° C.

Step E: Preparation of 10-hydroxamino-5-methylene-10,11-dihydro-5H-dibenzo[a,d]cycloheptene A mixture of 15.3 of oxime from Step D, 500 ml of methanol, 12 g of sodium cyanoborohydride in 450 ml of methanol was treated dropwise with a solution of 12 ml of 12N hydrochloric in 50 ml of methanol over 5 hours, and then stirred overnight at room temperature. The solvent was evaporated, the residue was stirred with 200 ml of 1N aqueous hydrochloric acid, made alkaline with concentrated ammonium hydroxide and extracted with 3×175 ml of ether. The combined extracts were dried (Na$_2$SO$_4$), filtered and evaporated. The crystalline residue was washed with methanol to give 9.6 g of 10-hydroxamino-5-methylene-10,11-dihydro-5H-dibenzo[a,d]cyclohepten, m.p. 145°–147° C.

Step F Preparation of 12-hydroxy-5-methyl-10,11-dihydro-5H-dibenzo[a,d]cyclohepten-5,10-imine A solution of 8.8 g of the hydroxamino compound from Step E in 200 ml of xylene was added dropwise to 80 ml of refluxing xylene. After 1 hour of refluxing the solvent was evaporated. The residue was treated with 250 ml of water and 7 ml of concentrated hydrochloric acid and the mixture was washed with 100 ml of ether and the wash was discarded. The aqueous phase was made basic with concentrated ammonium hydroxide and extracted with 3×100 ml of ether. The extract was dried (Na$_2$SO$_4$), filtered and evaporated. The residue was recrystallized from cyclohexane to give 8.5 g of 12-hydroxy-5-methyl-10,11-dihydro-5H-dibenzo[a,d]cyclohepten-5,10-imine, m.p. 141°–144° C.

Step G: Preparation of 5-methyl-10,11-dihydro-5H-dibenzo[a,d]cyclohepten-5,10-imine and oxalate salt A mixture of 1.2 g of the hydroxy-imine from Step F, 7 ml of acetic acid and 1.2 g of zinc dust was heated at 60°–70° C. for 3.5 hours. The mixture was filtered and the filter cake was washed with 200 ml of ether and 50 ml of water. The filtrate was made basic with 5% (w/v) aqueous sodium hydroxide and extracted with ether. The extract was dried (Na$_2$SO$_4$), filtered and evaporated to dryness to give 1.1 g of product. This material (1.1 g) was dissolved in 20 ml of acetone and treated with 0.6 g of oxalic acid in 10 ml of acetone. After cooling overnight, there was collected 1.2 g of 5-methyl-10,11-dihydro-5H-dibenzo[a,d]cyclhepten-5,10-imine oxalate, m.p. 203°–206° C. (dec.), which after recrystallization from methanol/acetone, had m.p. 215°–217° C. (dec.).

Employing the procedure substantially as described in Example 1 but substituting for the methyl lithium used in Step (B) thereof, an equimolecular amount of an organometallic of formula R$^2$CH$_2$-Li there are produced the 5-R$^2$CH$_2$-10,11-dihydro-5H-dibenzo[a,d]cyclohepten-5-10-imines where R$^2$ is —CH$_3$, —C$_2$H$_5$, —CH=CH$_2$,

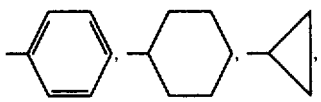

by the following reaction sequence.

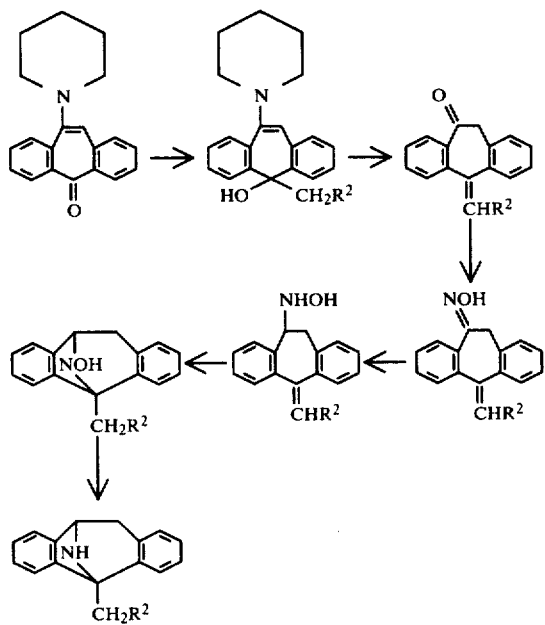

EXAMPLE 2

5-Ethyl-10,11-dihydro-5H-dibenzo[a,d]cyclohepten-5,10-imine

Step A Preparation of 5-ethylidene-10-oxo-10,11-dihydro-5H-dibenzo[a,d]cycloheptene To a stirred slurry of ethyltriphenylphosphonium bromide (21 g, 0.057 mole) in ether (400 ml) was added dropwise butyllithium in hexane (48 ml, 1.3 M). To the resulting solution was added a solution of 1-(5-keto-5H-dibenzo[a,d]cyclohepten-10-yl)-4-methylpiperazine (13.5 g, 0.044 mole) in THF (100 ml). The resulting mixture was stirred and heated under reflux for 3.5 hours, cooled and poured into ice $H_2O$ (300 ml). The organic phase was separated and the aqueous phase extracted with ether (2×150 ml). The combined organic solutions were concentrated under reduced pressure. The concentrate was stirred with a mixture of 1 N aqueous hydrochloric acid (300 ml) and ether (300 ml). The ether phase was separated, the aqueous phase extracted with ether, and the combined ether solutions dried over $Na_2SO_4$, filtered and the filtrate concentrated to 100 ml. Triphenylphosphine oxide was removed by filtration and the filtrate was chromatographed on silica-gel which was eluted with chloroform to yield 10.1 g (98%) of 5-ethylidene-10-oxo-10,11-dihydro-5H-dibenzo[a,d]cycloheptene, m.p. 93°–95° C.

Following the procedure substantially as described in Example 1, Steps D through G but substituting for the 5-methylene-10-oxo-10,11-dihydro-5H-dibenzo[a,d]cycloheptene used in Step D thereof, an equimolecular amount of 5-ethylidene-10-oxo-10,11-dihydro-5H-dibenzo[a,d]cycloheptene, there is produced in sequence:

5-ethylidene-10-hydroximino-10,11-dihydro-5H-dibenzo[a,d]cycloheptene, (86% yield), m.p. 128°–131° C.;

5-ethylidene-10-hydroxamino-10,11-dihydro-5H-dibenzo[a,d]cycloheptene (89% yield), m.p. 121°–124° C.;

5-ethyl-12-hydroxy-10,11-dihydro-5H-dibenzo[a,d]yclohepten-5,10-imine, (21% yield), m.p. 112°–116° C.; and 5-ethyl-10,11-dihydro-5H-dibenzo[a,d]cyclohepten-5,10-imine, (90% yield) and the hydrogen oxalate salt, m.p. 240°–241° C.

Employing the procedure substantially as described in Example 2 but substituting for the ethyltriphenylphosphonium bromide used in Step A, an equimolecular amount of a Wittig reagent of formula $(C_6H_5)_3P^+$-$CH_2R^2(Br^-)$, wherein —$CH_2R^2$ is —$CH_3$, —$CH_2CH_2CH_3$, or —$(CH_2)_3CH_3$, there are produced the compounds of formula:

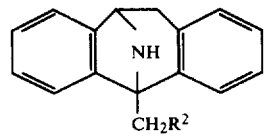

wherein —$CH_2R^2$ represents —$CH_3$, —$CH_2CH_2CH_3$ (m.p. 298°–299.5° C. as the HCl.½ $CH_3COCH_3$) and —$(CH_2)_3CH_3$.

EXAMPLE 3

5-(2-Hydroxyethyl)-10,11-dihydro-5H-dibenzo[a,d]cyclohepten-5,10-imine

Step A Preparation of 5-ethoxycarbonylmethylene-10,11-dihydro-5H-dibenzo[a,d]cyclohepten-10-one Triethylphosphonoacetate, 10 g (0.045 mole) was added dropwise to a slurry of 1.9 g (0.04 mole) of sodium hydride (50% in mineral oil) in 20 ml of dry toluene under nitrogen and keeping the temperature at 30°–35° C. by cooling. The mixture was stirred 1 hour at room temperature. A solution of 10 g (0.0328 mole) of 1-(5-keto-5H-dibenzo[a,d]cyclohepten-10-yl)-4-methylpiperazine in 75 ml of dry toluene was added dropwise, keeping the temperature at 25°–30° C. by cooling. The mixture was stirred at room temperature for 3 hours and held at room temperature overnight. After decanting the solution, the precipitate was washed with four 25 ml portions of toluene at 65° C. The combined toluene extracts were diluted with an equal volume of ether and shaken with 75 ml of 0.5N hydrochloric acid. The aqueous acid layer was separated and re-extracted with toluene-ether (1:1). The combined organic phases were washed with water, dried over magnesium sulfate, filtered, and concentrated. The oily solid obtained was freed from the bulk of the oil by collection on a sintered glass funnel and then triturated with cyclohexane to yield 4.5 g (47%) of 5-ethoxycarbonylmethylene-10,11-dihydro-5H-dibenzo[a,d]cyclohepten-10-one, m.p. 56°–62° C.

Step B Preparation of 5-ethoxycarbonylmethyl-10,12-dihydroxy-10,11-dihydro-5H-dibenzo[a,d]cyclohepten-5,10-imine The keto-olefin from Step A, 23.4 g (0.08 mole), together with hydroxylamine hydrochloride (6.0 g), sodium acetate trihydrate (12.0 g) and wet ether (300 ml) was stirred at room temperature. After 16 hours, the precipitate was collected, washed with ether, and stirred with water (300 ml) for 1 hour. The solid was collected and dried to obtain 21.6 g (83%) of 5-ethoxycarbonylmethyl-10,12-dihydroxy-10,11-dihydro-5H-dibenzo[a,d]cyclohepten-5,10-imine, m.p. 193°–195° C. dec.

Step C Preparation of 5-ethoxycarbonylmethyl-10-hydroxy-10,11-dihydro-5H-dibenzo[a,d]cyclohepten-5,10-imine The N-hydroxyimine from Step B, 21 g (0.0646 mole), was suspended in glacial acetic acid (125 ml) and zinc dust (16 g) was added in portions over 15 minutes. After the exothermic reaction had subsided, the mixture was stirred and heated in an oil bath at 65° C. for 3 hours. The cooled mixture was filtered and the filtrate was evaporated under reduced pressure. The residual syrup was dissolved in water (500 ml) and the filtered solution was made basic with 15% aqueous sodium hydroxide. The precipitate was collected, washed with water, and dried to yield 15 g of 5-ethoxycarbonylmethyl-10-hydroxy-10,11-dihydro-5H-dibenzo[a,d]cyclohepten-5,10-imine, m.p. 186°–189° C. dec. A filtered solution of this product in boiling acetone (350 ml) was treated with 7 N ethanolic hydrogen chloride (7 ml). The precipitate of the hydrochloride salt was collected, washed with ether, and dried to obtain 14.35 g (64%), m.p. 247°–250° C. dec.

Step D Preparation of 10-chloro-5-ethoxycarbonylmethyl-10,11-dihydro-5H-dibenzo[a,d]cyclohepten-5,10-imine The hydrochloride salt of the product from Step C, 17.8 g (0.0515 mole) was slurried in thionyl chloride (250 ml) and the mixture was heated to refluxing. After the ensuing exothermic reaction subsided the mixture was heated at reflux for 20 minutes when the solid had dissolved completely. The thionyl chloride was evaporated under reduced pressure and the last traces were removed by repeated co-evaporation with toluene. The residue was triturated with acetone and dried to give 15.35 g (81%), m.p. 223°–227° C. dec., of 10-chloro-5-ethoxycarbonylmethyl-10,11-dihydro-5H-dibenzo[a,d]cyclohepten-5,10-imine hydrochloride.

Step E Preparation of 5-(2-hydroxyethyl)-10,11-dihydro-5H-dibenzo[a,d]cyclohepten-5,10-imine The hydrochloride from Step D, 15.3 g (0.042 mole), was added in portions to a slurry of lithium aluminum hydride (5.6 g, 0.147 mole) in ether (200 ml) and tetrahydrofuran (200 ml). The mixture was stirred at reflux for 3 hours, then cooled to 0° C., and hydrolyzed by the dropwise addition of water (4 ml) and 10% aqueous sodium hydroxide (4 ml.). After dilution with ether, the precipitate was collected, suspended in chloroform (250 ml) and stirred at room temperature for 1 hour. The mixture was filtered and the filtrate was combined with the previously obtained ethereal filtrate. Solvents were evaporated under reduced pressure and the solid obtained was recrystallized from 95% ethanol to yield 8.6 g of 5-(2-hydroxyethyl)-10,11-dihydro-5H-dibenzo[a,d]cyclohepten-5,10-imine, m.p. 181°–184° C. Recrystallization from 70% ethanol gave m.p. 182°–184° C.

A suspension of this product (4.4 g) in warm absolute ethanol (20 ml) was treated with 7 N -ethanolic hydrogen chloride (2.5 ml) and the mixture was stirred until all of the solid dissolved. Dilution with ether precipitated the hydrochloride salt; 4.8 g, m.p. 263°–265° C. Recrystallization from acetonitrile gave m.p. 262°–264° dec.

EXAMPLE 4

3-(and 7)-Bromo-5-methyl-10,11-dihydro-5H-dibenzo[a,d]cyclohepten-5,10-imine

Step A Preparation of 3,10,11-tribromo-5H-dibenzo[a,d]cyclohepten-5-one

A solution of bromine (53 g., 0.33 mole) in glacial acetic acid (125 ml.) was added dropwise to a stirred slurry of 3-bromo-5H-dibenzo[a,d]cyclohepten-5-one (71.25 g., 0.25 mole) in glacial acetic acid (775 ml.). After the mixture had been stirred at room temperature for several hours, the solid was collected, washed with glacial acetic acid and dried; yield, 105.8 g. (95%), m.p. 173°–175° C.

Step B Preparation of 3,10-dibromo-5H-dibenzo[a,d]cyclohepten-5-one and 3,11-dibromo-3H-dibenzo[a,d]cyclohepten-5-one The product from Step A was added to a stirred solution of sodium hydroxide (28 g., 0.7 mole) in methanol (2 liter). The thick mixture was stirred at reflux for 1¼ hours. After cooling, the solid was collected, washed with methanol and then with water, and dried to obtain 81 g. (90%) of the mixture of 3,10-dibromo-5H-dibenzo[a,d]cyclohepten-5-one and 3,11-dibromo-5H-dibenzo[a,d]cyclohepten-5-one, m.p. 146°–156° C.

Step C Preparation of 3-bromo-10-(4-methylpiperazinyl)-5H-dibenzo[a,d]cyclohepten-5-one and 3-bromo-11-(4-methylpiperazinyl)-5H-dibenzo[a,d]cyclohepten-5-one Potassium tert-butoxide (6.8 g., 0.06 mole) was added to a stirred slurry of 3,10-dibromo-5H-dibenzo[a,d]cyclohepten-5-one and 3,11-dibromo-5H-dibenzo[a,d]cyclohepten-5-one (18.2 g., 0.05 mole), 4-methylpiperazine (10 ml.), and dry tert-butyl alcohol (200 ml.) at room temperature and under nitrogen. The dark orange mixture was heated to refluxing for 2 hours and then stirred at room temperature overnight. The mixture was poured into approximately 800 ml. of ice and water and extracted with ether. The ether extract was washed with water, dried over anhydrous sodium sulfate, filtered, and evaporated. The mixture of 3-bromo-10-(4-methylpiperazinyl)-5H-dibenzo[a,d]cyclohepten-5-one and 3-bromo-11-(4-methylpiperazinyl)-5H-dibenzo[a,d]cyclohepten-5-one was obtained as a residual red-yellow gum; yield, 19.4 g. 100%.

Step D Preparation of 3-bromo-5-methyl-10-(4-methylpiperazinyl)-5H-dibenzo[a,d]cyclohepten-5-ol and 3-bromo-5-methyl-11-(4-methylpiperazinyl)-5H-dibenzo[a,d]cyclohepten-5-ol Methyllithium, 35 ml. of a 1.6 M solution in ether, was added dropwise to a stirred solution of the product from Step C (18 g., 0.047 mole) in ether (200 ml) and tetrahydrofuran (60 ml) cooled in an ice bath and under nitrogen. Stirring was continued at room temperature for 3 hours. The mixture was cooled in ice and hydrolyzed by the dropwise addition of water. After dilution with ether and water, the layers were separated and the aqueous phase was re-extracted with ether. The combined ether extracts were washed with water, dried over anhydrous sodium sulfate and evaporated. The mixture of 3-bromo-5-methyl-10-(4-methylpiperazinyl)-5H-dibenzo[a,d]cyclohepten-5-ol and 3-bromo-5-methyl-11-(4-methylpiperazinyl)-5H-dibenzo[a,d]cyclohepten-5-ol was obtained as a residual dark yellow glass; yield, 18 g, (96%).

Step E Preparation of 3-bromo-5-methylene-10,11-dihydro-5H-dibenzo[a,d]cyclohepten-10-one and 7-bromo-5-methylene-10,11-dihydro-5H-dibenzo[a,d]cyclohepten-10-one A mixture of the product from Step D (18 g., 0.045 mole), 95% ethanol (80 ml.), 7N ethanolic hydrogen chloride (40 ml.), and 6N aqueous hydrochloric acid (80 ml.) was stirred at room temperature for 30 minutes and at reflux temperature for 1 hour. The mixture consisted of a brown oily lower phase and an aqueous alcoholic upper phase. The latter was decanted and the alcohol was stripped in vacuo. The residual aqueous mixture was extracted with chloroform. The previously obtained brown oil was dissolved in chloroform and the combined chloroform phases were washed with water and dried over anhydrous magnesium sulfate. Evaporation of the filtered extract left the crude product as a residual dark yellow glass. This material was chromatographed on a silica gel column, eluting with toluene. Evaporation of the approximately combined fractions left the partially purified product as an oily solid (8.5 g.). Trituration with cyclohexane afforded one of the isomers of the product as a white solid; yield, 2.6 g., m.p. 125°–158° C. Two recrystallizations from cyclohexane gave m.p. 158°–163° C. Evaporation of the first cyclohexane mother liquor left the remaining isomer of the product as a dark yellow oil. Trituration with three successive 10 ml. portions of hexane afforded a yellow solid; yield, 3.3 g., m.p. 75°–83° C. Two recrystallizations from hexane gave m.p. 84°–89° C.

The higher melting isomer (m.p. 160°–164° C.) has structural formula:

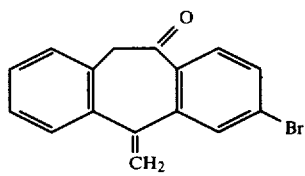

and is named 7-bromo-5-methylene-10,11-dihydro-5H-dibenzo[a,d]cyclohepten-10-one.

The other isomer, 3-bromo-5-methylene-10,11-dihydro-5H-dibenzo[a,d]cyclohepten-10-one (m.p. 84°–91° C.) has structural formula:

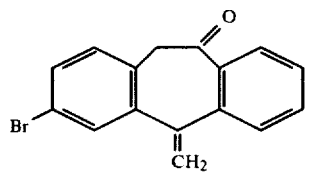

Step F through I Preparation of 3(and 7)-bromo-5-methyl-10,11-dihydro-5H-dibenzo[a,d]cyclohepten-5,10-imine Employing the procedure substantially as described in Example 1, Steps D through G, but substituting for the 5-methylene-10-oxo-10,11-dihydro-5H-dibenzo[a,d]cycloheptene employed therein, an equimolecular amount of the corresponding 3- and 7-bromo- compounds there is produced in sequence, the following:

(Step F) 3(and 7)-bromo-10-hydroximino-5-methylene-10,11-dihydro-5H-dibenzo[a,d]cycloheptene, m.p.'s 171°–175° C. and 179°–181° C. respectively;

(Step G) 3(and 7-bromo-10-hydroxamino-5-methylene-10,11-dihydro-5H-dibenzo[a,d]cycloheptene, m.p.'s 149°–153° C. and 136°–139° C. respectively;

(Step H) 3(and 7)-bromo-12-hydroxy-5-methyl-10,11-dihydro-5H-dibenzo[a,d]cyclohepten-5,10-imine, m.p.'s 175°–180° C. and 187°–189° C. respectively; and (Step I) 3(and 7)-bromo-5-methyl-10,11-dihydro-5H-dibenzo[a,d]cyclohepten-5,10-imine hydrochloride, m.p.'s >300° C.

Employing the procedure substantially as described in Example 4 but substituting for the 3-bromo-10,11-dihydro-5H-dibenzo[a,d]cycloheptene used in Step A thereof and for the methyl lithium used in Step D thereof, a 2,3,7 or 8-X-10,11-dihydro-5H-dibenzo[a,d]cycloheptene and an organometallic of formula $R^2CH_2$-Li or a Wittig reagent of formula $(C_6H_5)_3P^+$-$CH_2R^2(Br^-)$ as used in Example 2, Step A described in Table I there are produced the 2,3,7 or 8-X-5-$R^2CH_2$-10,11-dihydro-5H-dibenzo[a,d]cyclohepten-5,10-imines, also described in Table I in accordance with the following reaction sequence:

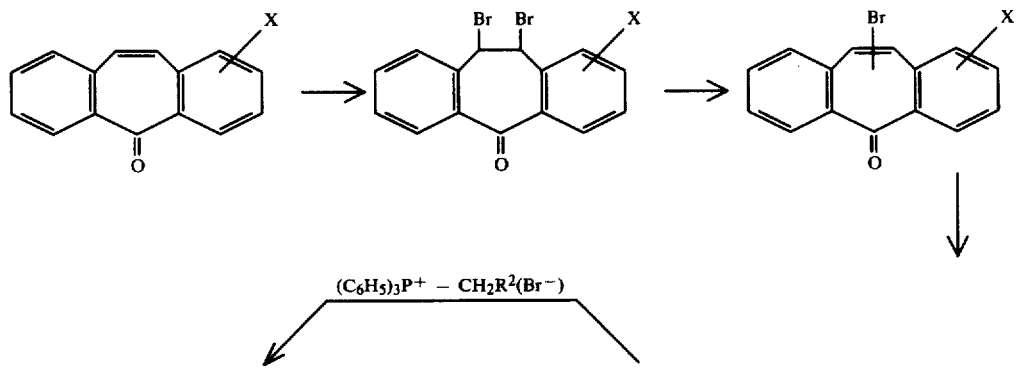

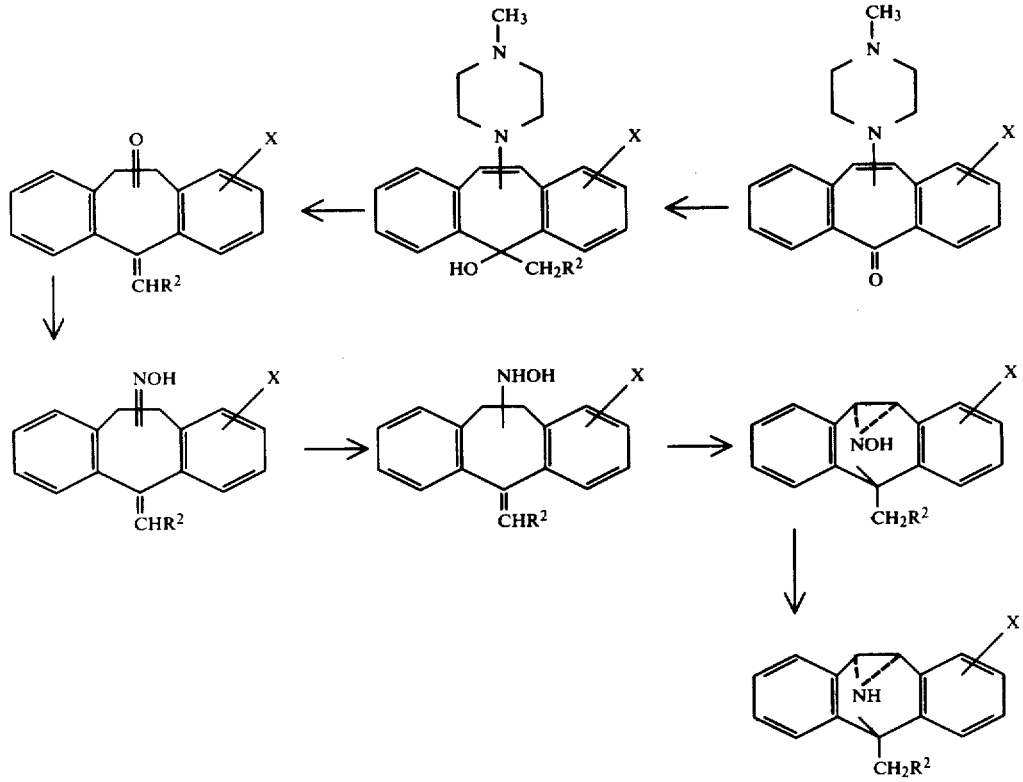

wherein X is chloro, bromo, fluoro or iodo, and the partial bonds to the bridge-ring nitrogen atom is representative of a bond to either the 10-or 11- position.

TABLE I

| R² | X |
|---|---|
| CH₃ | 8-Br |
| —C₂H₅ | 3-Br |
| —CH=CH₂ | 3-Br |
| —⌬ (phenyl) | 3-Br |
| —⌬ (cyclohexyl) | 3-Br |
| —⊲ (cyclopropyl) | 3-Br |
| —CH₃ | 7-Br |
| —C₂H₅ | 7-Br |
| —CH=CH₂ | 7-Br |
| —⌬ (phenyl) | 7-Br |
| —⌬ (cyclohexyl) | 7-Br |
| —⊲ (cyclopropyl) | 7-Br |
| —H | 8-Br |
| —CH₃ | 3-Cl |
| —C₂H₅ | 3-F |
| —CH=CH₂ | 3-I |

TABLE I-continued

| R² | X |
|---|---|
| —⌬ (phenyl) | 3-Cl |
| —⌬ (cyclohexyl) | 3-F |
| —⊲ (cyclopropyl) | 3-I |
| —H | 7-F |
| —CH₃ | 7-Cl |
| —C₂H₅ | 7-F |
| —CH=CH₂ | 7-I |
| —⌬ (phenyl) | 7-Cl |
| —⌬ (cyclohexyl) | 7-F |
| —⊲ (cyclopropyl) | 7-I |

EXAMPLE 5

10,11-Dihydro-5,12-dimethyl-5H-dibenzo[a,d]cyclohepten-5,10-imine fumaric acid salt Step A: Preparation of 10,11-dihydro-12-ethoxycarbonyl-5-methyl-5H-dibenzo[a,d]cyclohepten-5,10-imine A mixture of 1.15 g. of 10,11-dihydro-5-methyl-5H-dibenzo[a,d]cyclohepten-5,10-imine, 1.0 g of anhydrous sodium carbonate, 1 ml of ethyl chloroformate and 10 ml of dry benzene was stirred at reflux temperature for 2 hours. The mixture was filtered and the filtrate was evaporated in vacuo to give 1.45 g of white crystalline 10,11-dihydro-12-ethoxycarbonyl-5-methyl-5H-dibenzo[a,d]cyclohepten-5,10-imine, m.p. 80°-83° C.

Step B: Preparation of 10,11-dihydro-5,12-dimethyl-5H-dibenzo[a,d]cyclohepten-5,10-imine A solution of the urethan from Step A in 15 ml of absolute ether was added dropwise to a slurry of 190 mg of lithium aluminum hydride in 15 ml of absolute ether with stirring and under nitrogen. After 24 hours at room temperature, the mixture was cooled in an ice bath and hydrolyzed by the dropwise addition of the minimum volume of water containing a few drops of 5% (w/v) aqueous sodium hydroxide. After dilution with ether, the mixture was filtered. The filtrate was evaporated in vacuo to give 1.1 g of the free base of the product as a colorless oil. This was combined with 0.9 g of similar material and dissolved in 25 ml of ethyl acetate. A warm solution of 1.2 g of fumaric acid in 12 ml of methanol was added. The fumaric acid salt which crystallized was collected and was recrystallized from methanol-ethyl acetate to give 2.1 g of 10,11-dihydro-5,12-dimethyl-5H-dibenzo[a,d]cyclohepten-5,10-imine fumaric acid salt, m.p. 186°-188° C.

EXAMPLE 6

12-Benzyl-10,11-dihydro-5-methyl-5H-dibenzo[a,d]cyclohepten-5,10-imine

A mixture of 2.45 g of 10,11-dihydro-5-methyl-5H-dibenzo[a,d]cyclohepten-5,10-imine, 1.9 g of benzyl chloride, 3.2 g of anhydrous sodium carbonate and 50 ml of dry benzene was stirred at reflux temperature for 4 days. The mixture was filtered and the filtrate was evaporated in vacuo to give 3.1 g of the product as an oily solid, m.p. 107°-111° C. This was recrystallized twice from 95% ethanol to give 1.85 g of white crystalline 12-benzyl-10,11-dihydro-5-methyl-5H-dibenzo[a,d]cyclohepten-5,10-imine, m.p. 111°-114° C.

EXAMPLE 7

12-Allyl-10,11-dihydro-5-methyl-5H-dibenzo[a,d]cyclohepten-5,10-imine

A mixture of 2.45 g of 10,11-dihydro-5-methyl-5H-dibenzo[a,d]cyclohepten-5,10-imine, 1.8 g of allyl bromide, 3.0 g of anhydrous sodium carbonate and 50 ml of dry benzene was stirred at reflux temperature for 20 hours. The mixture was filtered and the filtrate was evaporated in vacuo to give 1.2 g of the oily free base of the product. This was dissolved in 5 ml of acetone and added to a warm solution of 0.75 g of fumaric acid in 75 ml of acetone. The salt which crystallized was collected and recrystallized from acetone to give 1.45 g of white crystalline 12-allyl-10,11-dihydro-5-methyl-5H-dibenzo[a,d]cyclohepten-5,10-imine fumaric acid salt, m.p. 180°-182° C.

Employing the procedure of Example 7, but substituting for the allyl bromide and the 10,11-dihydro-5-methyl-5H-dibenzo[a,d]cyclohepten-5,10-imine used therein a compound of formula R-I and 5-$R^2CH_2$10,11-dihydro-5H-dibenzo[a,d]cyclohepten-5,10-imine, described in Table II, there are produced the 5-$R^2CH_2$-12-R-10,11-dihydro-5H-dibenzo[a,d]cyclohepten-5,10-imines also described in Table II, in accordance with the following reaction:

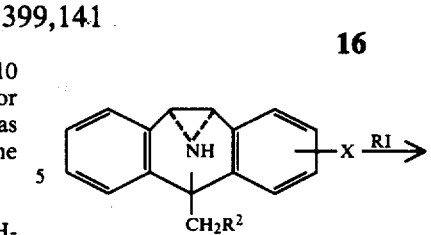

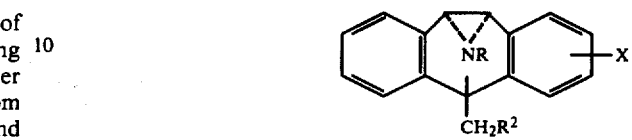

wherein X is -H, -Cl, -Br, -F, -I.

TABLE II

| $R^2$ | R | X |
|---|---|---|
| —H | —$C_2H_5$ | H |
| —$CH_3$ | —$C_2H_5$ | H |
| —$C_2H_5$ | cyclopropyl | H |
| —CH=$CH_2$ | cyclohexyl | H |
| phenyl | —$CH_3$ | H |
| cyclohexyl | —$CH_3$ | H |
| cyclopropyl | —$CH_3$ | H |
| —$CH_3$ | —$CH_2CH=CH_2$ | H |
| —H | —$CH_3$ | 3-Br |
| —$CH_3$ | —$C_2H_5$ | 8-Br |
| —$C_2H_5$ | cyclopropyl | 3-Br |
| —CH=$CH_2$ | cyclohexyl | 3-Br |
| phenyl | —$CH_3$ | 3-Br |
| cyclohexyl | —$CH_3$ | 3-Br |
| cyclopropyl | —$CH_3$ | 3-Br |
| —H | —$CH_2CH=CH_2$ | 3-Br |
| —H | —$CH_3$ | 8-Br |
| —$CH_3$ | —$C_2H_5$ | 7-Br |
| —$C_2H_5$ | cyclopropyl | 7-Br |
| —CH=$CH_2$ | cyclohexyl | 7-Br |
| phenyl | —$CH_3$ | 7-Br |

TABLE II-continued

| R² | R | X |
|---|---|---|
| cyclohexyl | —CH₃ | 7-Br |
| cyclopropyl | —CH₃ | 7-Br |
| —H | —CH₂CH=CH₂ | 7-Br |
| —H | —CH₂—C₆H₄—Cl (ortho) | H (m.p. 132.5–135.5° C.) |
| —H | —CH₂—C₆H₄—Cl (para) | H (m.p. 111–113° C. hydrogen oxalate) |
| —H | —CH₂—C₆H₄—CH₃ | H |
| —H | —CH₂CH₂—C₆H₅ | H (m.p. 115.5–117° C.) |
| —CH₃ | —CH₂—C₆H₅ | H (m.p. 163–164° C.) |
| —CH₂CH₃ | —CH₂—C₆H₅ | H (m.p. 132.5–135.5° C.) |
| H | —CH₂—C₆H₄—Cl | H (m.p. 112–114.5° C.) |
| H | —CH₂—C₆H₅ | H (m.p. 111–113° C., base) |
| H | —CH₃ | 3-F |
| —CH₃ | —CH₃ | 3-Cl |
| —C₂H₅ | —CH₃ | 3-F |
| —C=CH₂ | —CH₃ | 3-I |
| phenyl | —CH₃ | 3-Cl |
| cyclohexyl | —CH₃ | 3-F |
| cyclopropyl | —CH₃ | 3-I |
| —H | —CH₃ | 7-F |
| —CH₃ | —CH₃ | 7-Cl |
| —C₂H₅ | —CH₃ | 7-F |
| —CH=CH₂ | —CH₃ | 7-I |
| phenyl | —CH₃ | 7-Cl |
| cyclohexyl | —CH₃ | 7-F |
| cyclopropyl | —CH₃ | 7-I |

EXAMPLE 8

3-Methoxy-5-methyl-10,11-dihydro-5H-dibenzo[a,d]cyclohepten-5,10-imine

A mixture of 0.00905 mol of 3-bromo-5-methyl-10,11-dihydro-5H-dibenzo[a,d]cyclohepten-5,10-imine, 0.181 mol of sodium methoxide, 5.56 g of electrolytic copper dust, and 87 ml of DMF is stirred and heated on a steam bath for 2.5 hours. After cooling, 150 ml of water and 150 ml of ether is added to the mixture, and, after stirring, the mixture is filtered through a pad of celite. The ether phase is separated, washed with water, dried over magnesium sulfate, filtered, and the ether is removed on a rotary evaporator. The residue is dissolved in warm acetonitrile. On standing, the solution deposits crystals. The supernatant, containing the desired product, is decanted from the crystals. Evaporation of the solvent gives 3-methoxy-5-methyl-10,11-dihydro-5H-dibenzo[a,d]cyclohepten-5,10-imine.

Employing the procedure substantially as described in Example 8, but substituting for the 3-bromo-5-methyl-10,11-dihydro-5H-dibenzo[a,d]cyclohepten-5,10-imine and sodium methoxide used therein, equimolecular amounts, respectively, of the 2,3,7 or 8-bromo-compounds and sodium lower alkoxides described in Table III, there are produced the 2,3,7 or 8-lower alkoxy-compounds also described in Table III in accordance with the following reaction:

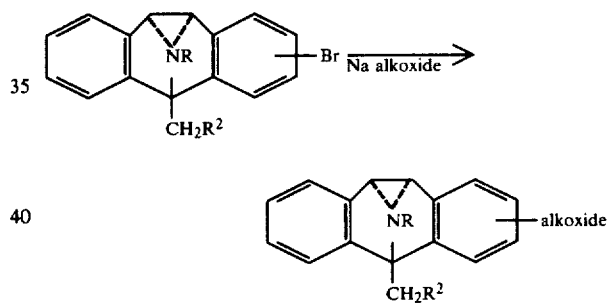

TABLE III

| R | R² | alkoxide |
|---|---|---|
| H | H | 7-OCH₃ |
| H | —CH₃ | 3-OC₂H₅ |
| H | —C₂H₅ | 3-OCH₃ |
| H | —CH=CH₂ | 3-OCH₃ |
| H | phenyl | 3-OC₂H₅ |
| H | cyclohexyl | 3-OCH₃ |
| H | cyclopropyl | 3-OC₂H₅ |
| H | —CH₃ | 7-OCH₃ |
| H | —C₂H₅ | 7-OC₂H₅ |
| H | —CH=CH₂ | 7-OCH₃ |
| H | phenyl | 7-OCH₃ |

TABLE III-continued

| R | R² | alkoxide |
|---|---|---|
| H | —⟨phenyl⟩ | 7-OCH₃ |
| H | —⟨cyclopropyl⟩ | 7-OCH₃ |
| —CH₃ | —H | 3-OCH₃ |
| —C₂H₅ | —CH₃ | 8-OCH₃ |
| —⟨cyclopropyl⟩ | —C₂H₅ | 3-OCH₃ |
| —⟨phenyl⟩ | —CH=CH₂ | 3-OCH₃ |
| —CH₃ | —⟨phenyl⟩ | 3-OCH₃ |
| —CH₃ | —⟨cyclohexyl⟩ | 3-OCH₃ |
| —CH₃ | —⟨cyclopropyl⟩ | 3-OCH₃ |
| CH₂CH=CH₂ | H | 3-OC₃H₇ |
| —CH₃ | —H | 8-OCH₃ |
| —C₂H₅ | —CH₃ | 7-OCH₃ |
| —⟨cyclopropyl⟩ | —C₂H₅ | 7-OC₂H₅ |
| —⟨phenyl⟩ | —CH=CH₂ | 7-OCH₃ |
| —CH₃ | —⟨phenyl⟩ | 7-OC₂H₅ |
| —CH₃ | —⟨cyclohexyl⟩ | 7-OCH₃ |
| —CH₃ | —⟨cyclopropyl⟩ | 7-OC₃H₅ |
| —CH₂CH=CH₂ | —H | 7-OCH₃ |

EXAMPLE 9

3-Cyano-5-methyl-10,11-dihydro-5H-dibenzo[a,d]cyclohepten-5,10-imine

A mixture of 0.0249 mol of 3-bromo-5-methyl-10,11-dihydro-5H-dibenzo[a,d]cyclohepten-5,10-imine, 4.58 gm (0.0498 mol) of cuprous cyanide, and 30 ml of dry dimethylformamide is stirred and heated under reflux for 6.5 hours. To the cooled solution (25° C.) is added 54 ml of water, 27 ml of a saturated aqueous solution of sodium cyanide, and 75 ml of benzene. The mixture is stirred until a two phase system is obtained. The benzene phase is removed and the aqueous phase is extracted with two 75 ml portions of benzene. The combined benzene phases are washed with 100 ml of aqueous 0.1 M sodium cyanide, three 100 ml portions of water, and dried over magnesium sulfate. After filtering, evaporation of the benzene gives a crystalline residue which is dissolved in the minimum volume of chloroform and passed over an alumina column (15"×1") packed in chloroform. The column is eluted with chloroform. Evaporation of the eluate provides 3-cyano-5-methyl-10,11-dihydro-5H-dibenzo[a,d]cyclohepten-5,10-imine.

Employing the procedure substantially as described in Example 9, but substituting for the 3-bromo-5-methyl-10,11-hydro-5H-dibenzo[a,d]cyclohepten-5,10-imine used therein, an equimolecular amount of the bromo-compounds described in Table IV, there are produced the cyano-compounds also described in Table IV in accordance with the following reaction:

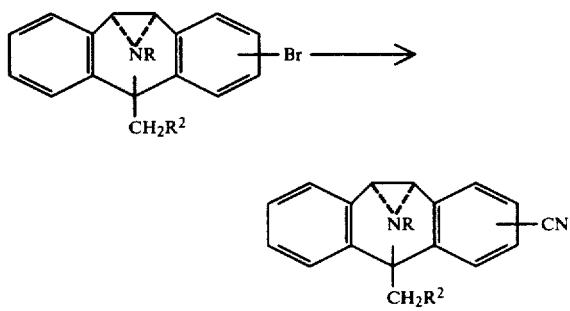

TABLE IV

| R | R² | —CN Position |
|---|---|---|
| —H | —CH₃ | 7 |
| —H | —C₂H₅ | 7 |
| —H | —CH₂=CH₂ | 7 |
| —H | —⟨phenyl⟩ | 7 |
| —H | —⟨cyclohexyl⟩ | 7 |
| —H | —⟨cyclopropyl⟩ | 7 |
| —CH₃ | —H | 8 |
| —C₂H₅ | —CH₃ | 8 |
| —⟨cyclopropyl⟩ | —C₂H₅ | 3 |
| —⟨phenyl⟩ | —CH=CH₂ | 3 |
| —CH₃ | —⟨phenyl⟩ | 3 |
| —CH₃ | —⟨cyclohexyl⟩ | 3 |
| —CH₃ | —⟨cyclopropyl⟩ | 3 |
| —CH₂CH=CH₂ | H | 3 |

EXAMPLE 10

3-Carboxy-5-methyl-10,11-dihydro-5H-dibenzo[a,d]cyclohepten-5,10-imine

A mixture of 0.00318 mol of 3-cyano-5-methyl-10,11-dihydro-5H-dibenzo[a,d]cyclohepten-5,10-imine and 20 ml of 6 N hydrochloric acid is stirred and refluxed for 18 hours. After cooling, the mixture is filtered, and the collected solid is washed with 6 N hydrochloric acid and then with ethanol and dried to give 3-carboxy-5-methyl-10,11-dihydro-5H-dibenzo[a,d]cyclohepten-5,10-imine.

Employing the procedure substantially as described in Example 10, but substituting for the 3-cyano-5-methyl-10,11-dihydro-5H-dibenzo[a,d]cyclohepten-5,10-imine used therein, an equimolecular amount of the cyano-compounds described in Table V, there are produced the carboxy-compounds described in Table V in accordance with the following reaction:

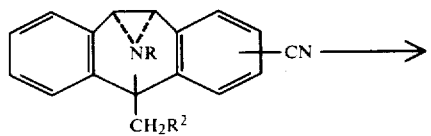

TABLE V

| R | $R^2$ | —COOH Position |
|---|---|---|
| —H | —$CH_3$ | 7 |
| —H | —$C_2H_5$ | 7 |
| —H | —$CH_2$=$CH_2$ | 7 |
| —H | —⌬(phenyl) | 7 |
| —H | —⌬(cyclohexyl) | 7 |
| —H | —⌬(cyclopropyl) | 7 |
| —$CH_3$ | —H | 8 |
| —$C_2H_5$ | —$CH_3$ | 8 |
| —⌬(cyclopropyl) | —$C_2H_5$ | 3 |
| —⌬(cyclohexyl) | —$CH_2CH_2$ | 3 |
| —$CH_3$ | —⌬(phenyl) | 3 |
| —$CH_3$ | —⌬(cyclohexyl) | 3 |
| —$CH_3$ | —⌬(cyclopropyl) | 3 |

TABLE V-continued

| R | $R^2$ | —COOH Position |
|---|---|---|
| —$CH_2CH$=$CH_2$ | H | 3 |

EXAMPLE 11

3-Trifluoromethylthio-5-methyl-10,11-dihydro-5H-dibenzo[a,d]cyclohepten-5,10-imine A mixture of 2.24 g (0.0353 mol) of copper dust, 3.90 g (0.97 mol) of bis-(trifluoromethylthio)mercury, (0.00484 mol) of 3-bromo-5-methyl-5,10-dihydro-5H-dibenzo[a,d]cyclohepten-5,10-imine and 20 ml of dimethylformamide is stirred and heated under reflux for six hours. The mixture is cooled in an ice bath and 100 ml of chloroform and 30 ml of concentrated ammonium hydroxide are added. The mixture is stirred overnight at room temperature and is filtered through a pad of diatomaceous earth. The filtrate and chloroform washings are combined and separated from the aqueous phase. The chloroform phase is washed with water, dried over magnesium sulfate, filtered, and the chloroform is removed on a rotary evaporator to give 3-trifluoromethylthio-5-methyl-10,11-dihydro-5H-dibenzo[a,d]cyclohepten-5,10-imine.

Employing the procedure substantially as described in Example 11, but substituting for the 3-bromo-5-methyl-10,11-dihydro-5H-dibenzo[a,d]cyclohepten-5,10-imine used therein, equimolecular amounts of the bromo-compounds described in Table VI, there are produced the trifluoromethylthio-compounds also described in Table VI in accordance with the following reaction:

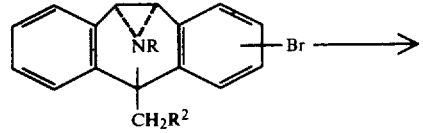

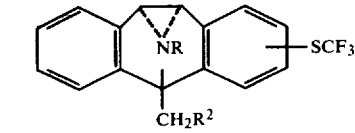

TABLE VI

| R | $R^2$ | —$SCF_3$ Position |
|---|---|---|
| —H | —$CH_3$ | 7 |
| —H | —$C_2H_5$ | 7 |
| —H | —$CH_2$=$CH_2$ | 7 |
| —H | —⌬(phenyl) | 7 |
| —H | —⌬(cyclohexyl) | 7 |
| —H | —⌬(cyclopropyl) | 7 |
| —$CH_3$ | —H | 8 |
| —$C_2H_5$ | —$CH_3$ | 8 |

TABLE VI-continued

| R | R² | —SCF₃ Position |
|---|---|---|
|  | —C₂H₅ | 3 |
|  | —CH₂CH₂ | 3 |
| —CH₃ |  | 3 |
| —CH₃ |  | 3 |
| —CH₃ |  | 3 |
| —CH₂CH=CH₂ | H | 3 |

EXAMPLE 12
8-Hydroxy-5,12-dimethyl-10,11-dihydro-5H-dibenzo[a,d]cyclohepten-5,10-imine A mixture of 8-methoxy-5,12-dimethyl-10,11-dihydro-5H-dibenzo[a,d]cyclohepten-5,10-imine (2.5 g) and freshly fused pyridine hydrochloride (25 g) is heated at 210° C. for 20 minutes. The cooled mixture is slurried with water and the pH adjusted to 8.5 with concentrated ammonium hydroxide. The aqueous mixture is extracted with chloroform. The chloroform extract is washed with water, dried over Na₂SO₄, filtered and evaporated. Chromatography of the concentrate on silica gel eluted with chloroform gives 8-hydroxy-5,12-dimethyl-10,11-dihydro-5H-dibenzo[a,d]cyclohepten-5,10-imine.

Employing the procedure substantially as described in Example 12 but substituting for the 8-methoxy compound used therein equimolecular amounts of the alkoxy compounds described in Table III, there are produced the corresponding hydroxy compounds described in Table VII in accordance with the following reaction:

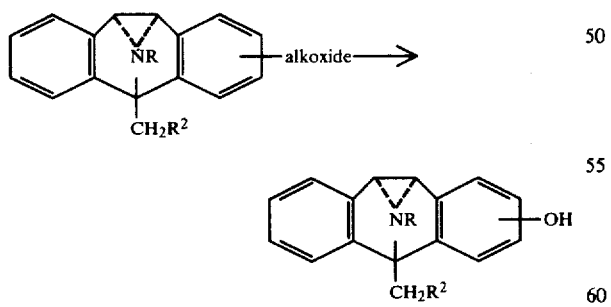

TABLE VII

| R | R² | —OH |
|---|---|---|
| H | H | 7 |
| H | —CH₃ | 3 |
| H | —C₂H₅ | 3 |
| H | —CH=CH₂ | 3 |
| H |  | 3 |
| H |  | 3 |
| H |  | 3 |
| H | —CH₃ | 7 |
| H | —C₂H₅ | 7 |
| H | —CH=CH₂ | 7 |
| H |  | 7 |
| H |  | 7 |
| H |  | 7 |
| —CH₃ | —H | 3 |
| —C₂H₅ | —CH₃ | 8 |
|  | —C₂H₅ | 3 |
|  | —CH=CH₂ | 3 |
| —CH₃ |  | 3 |
| —CH₃ |  | 3 |
| —CH₃ |  | 3 |
| CH₂CH=CH₂ | H | 3 |
| —C₂H₅ | —CH₃ | 7 |
|  | —C₂H₅ | 7 |
|  | —CH=CH₂ | 7 |
| —CH₃ |  | 7 |
| —CH₃ |  | 7 |
| —CH₃ |  | 7 |
| —CH₂CH=CH₂ | —H | 7 |

EXAMPLE 13

5,10,12-Trimethyl-10,11-dihydro-5H-dibenzo[a,d]cycloheptene-5,10-imine hydrochloride Step A: Preparation of 10-amino-5-methylene-10,11-dihydro-5H-dibenzo[a,d]cycloheptene To a stirred slurry of zinc dust (0.9 g, 0.138 mole) in 100 ml of glacial acetic acid stirred in an oil bath at 65° was added 10-hydroxyamino-5-methylene-10,11-dihydro-5H-dibenzo[a,d]cycloheptene (10 g, 42 mmole). The mixture was stirred in the oil bath for 2 hours, cooled, and quenched in 500 ml of water. The mixture was made basic with concentrated ammonia, then extracted with ether. The combined ether layers were washed with water, dried over sodium sulfate, filtered, and evaporated to dryness in vacuo. The residue was recrystallized from hexane to give 7.8 g, m.p. 84.5°–86.5°.

Step B: Preparation of 10-isocyano-5-methylene-10,11-dihydro-5H-dibenzo[a,d]cycloheptene To a solution of 10-amino-5-methylene-10,11-dihydro-5H-dibenzo[a,d]cycloheptene (8.1 g, 36.6 mmole) in chloroform (180 ml) was added sodium hydroxide pellets (4.42 g, 0.11 mole) benzyltriethylammonium chloride (0.42 g, 1.8 mmole) and water (0.5 ml). The mixture was stirred under nitrogen until the sodium hydroxide pellets dissolved (ca 4 hours), treated with anhydrous potassium carbonate, filtered, and evaporated to dryness in vacuo. The resulting oil was dissolved in chloroform (180 ml), treated with another 1.5 g (37.5 mmole) of sodium hydroxide and 0.2 g (0.86 mmole) of benzyltriethylammonium chloride, and stirred overnight under nitrogen. The mixture was again dried over potassium carbonate, filtered, and evaporated to dryness in vacuo. The resulting oil was chromatographed on 120 g of silica gel, and eluted with methylene chloride. The combined product fractions were evaporated to dryness in vacuo and the resulting solid was recrystallized from ether to give 4 g of solid, m.p. 96°–98°.

Step C: Preparation of 10-isocyano-10-methyl-5-methylene-10,11-dihydro-5H-dibenzo[a,d]cycloheptene Diisoproylamine (1.1 g, 10.9 mmole) in 25 ml of dry tetrahydrofuran was stirred in a dry ice/acetone bath. Under a nitrogen blanket, this solution was treated with n-butyllithium/hexane (5.0 ml of 2.2 M solution) added dropwise over 10 minutes. After 5 minutes, a solution of 10-isocyano-5-methylene-10,11-dihydro-5H-dibenzo[a,d]cycloheptene (2.4 g, 10.4 mmole) in 25 ml of dry tetrahydrofuran was added dropwise (over 45 minutes) to the lithium diisopropylamide solution. The resulting deep red solution was stirred in the cold for 15 minutes then treated with methyliodide (4.56 g, 32 mmole) added all at once. The mixture was stirred 2 hours in the cold and an additional 1 hour at room temperature. The solvent was removed in vacuo and the residue chromatographed on 75 g of silica gel, eluted with methylene chloride. The combined product fractions were evaporated in vacuo to give 2.2 g (86%) solid. Recrystallization from ether gave, m.p. 146°–147.5° C.

Step D: Preparation of 10-methyl-10-methylamino-5-methylene-10,11-dihydro-5H-dibenzo[a,d]cycloheptene hydrogen chloride 10-isocyano-10-methyl-5-methylene-10,11-dihydro-5H-dibenzo[a,d]cycloheptene (1.8 g, 7.3 mmole), dissolved in dry ether (100 ml) was added dropwise to a slurry of lithium tetrahydridoaluminate (0.53 g, 14 mmole) in ether (40 mmole) stirred under nitrogen. The mixture was heated at reflux for 1 hour, cooled, and the excess hydride decomposed by careful dropwise addition of 1.5 ml of ice water. The suspension was filtered and the solids washed twice with ether. The combined ether fractions were evaporated in vacuo to 1.8 g of oil. This oil, dissolved in 10 ml of absolute ethanol was treated with a slight excess of 8 N ethanolic HCl and cooled to give 1.7 g (81%) of powder, m.p. 238°–240°(d).

Step E: Preparation of 5,10,12-trimethyl-10,11-dihydro-5H-dibenzo[a,d]cyclohepten-5,10-imine hydrogen chloride 10-Methyl-10-methylamino-5-methylene-10,11-dihydro-5H-dibenzo[a,d]cycloheptene (1.6 g, 6.4 mmole) was dissolved in dry tetrahydrofuran (40 ml). To this solution, stirred at room temperature under nitrogen, was added n-BuLi (3.0 ml of a 2.2 M solution in hexane) dropwise over 5 minutes. The mixture was stirred 10 minutes, then treated with 3 ml of ice water. The tetrahydrofuran was removed under vacuum and the residue taken up in ether. The ether solution was washed with water, dried over sodium sulfate, filtered, and evaporated to dryness in vacuo. The resulting oil was chromatographed on 120 g of silica gel, eluted with methylene chloride and 1%, 1.5%, 2%, 3%, and 5% methanol in methylene chloride.

The combined product fractions were evaporated to dryness in vacuo, dissolved in 50 ml of absolute ethanol, and treated with a slight excess of 8 N ethanolic HCl. The solvent was removed in vacuo and the residual solid recrystallized from 20 ml of absolute ethanol to give 5,10,12-trimethyl-10,11-dihydro-5H-dibenzo [a,d]cyclohepten-5,10-imine hydrogen chloride, m.p. 295°–296.5° C.

Employing the procedure substantially as described in Example 13, but substituting for the 5-methylene compound used in Step A and the methyl iodide used in Step C thereof, the 5-(=CHR²)-compounds and R¹-iodides respectively described in Table VIII, there are produced the dibenzocyclohepten-5,10-imines also described in Table VII in accordance with the following reaction scheme:

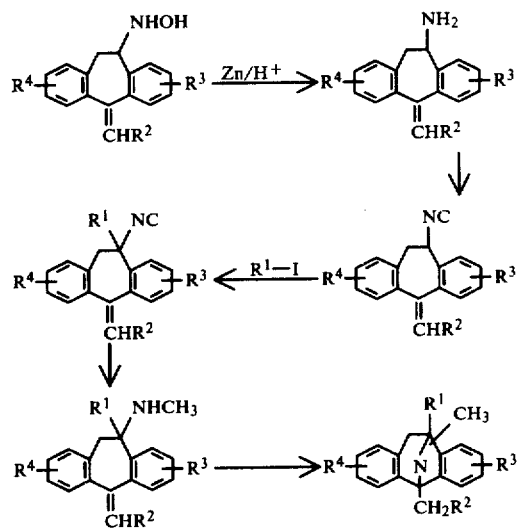

TABLE VIII

| R¹ | R² | R³ | R⁴ |
| --- | --- | --- | --- |
| —CH₂—CH=CH₂ | H | H | H |

TABLE VIII-continued

| R¹ | R² | R³ | R⁴ |
|---|---|---|---|
| −CH₂−⟨phenyl⟩ | CH₃ | H | H |
| −⟨phenyl⟩ | H | H | H |
| −CH₂−⟨cyclopropyl⟩ | H | H | H |

EXAMPLE 14

Resolution of (±)-5-Methyl-10,11-dihydro-5H-dibenzo[a,d]cyclohepten-5,10-imine

Levorotatory isomer: To a solution of 66.1 g (0.299 mole) of racemic 5-methyl-10,11-dihydro-5H-dibenzo[a,d]cyclohepten-5,10-imine in 107 ml of warm acetone is added 115.4 g (0.299 mole) of di-p-toluoyl-d-tartaric acid dissolved in 163 ml acetone. The solution is stirred until homogeneous, allowed to stand 18 hours at 25° C., then cooled in the freezer to 0° C. for 4 hours. The salt that forms is removed by filtration, washed once with cold acetone, collected and dried at 50° C. (vacuum oven) to give 82.97 g of A as a white solid, $[\alpha]_{589}{}^D = -125.9°$ (abs. EtOH), m.p. 141°-146° C. (foam). The filtrate of solid A is concentrated to dryness in vacuo and the solid residue B used in the preparation of the dextrorotatory isomer (see below).

Salt A is dissolved in 3450 ml of boiling acetone, filtered, concentrated to 1500 ml, allowed to stand 18 hours at 25° C., then cooled in the freezer to 0° C. for 4 hours. The precipitate is removed by filtration, washed once with cold acetone, collected and dried at 60° C. (vacuum oven) to give 45.5 g of C as a white solid, $[\alpha]_{589}{}^D = -131.9°$ (abs. EtOH), m.p. 142°-144° C. (foam).

The resolved salt C (44.8 g, 0.0737 mol) is treated with 300 ml of 10% sodium hydroxide and 300 ml of diethyl ether and the mixture stirred until the solid is dissolved. The ether layer is separated, dried over MgSO₄, filtered, and evaporated to dryness in vacuo to prodice 16.0 g of a tlc (silica GF eluted with 1:9 methanol:chloroform) homogeneous colorless oil. Crystallization from 40 ml of cyclohexane gives 14.16 g of (−)-5-methyl-10,11-dihydro-5H-dibenzo[a,d]cyclohepten-5,10-imine as a white solid, $[\alpha]_{589} = -160.8°$, (C=0.032 g/2 ml ethanol), m.p. 68.5°-69.5° C.

Dextrorotatory isomer: Residue B from the preparation of the levorotatory isomer was converted to free base form by stirring with 300 ml of 10% sodium hydroxide and 300 ml of diethyl ether until the solid is dissolved. The ether layer is dried over MgSO₄, filtered, and the solvent removed under reduced pressure to give 37.9 g of an orange oil which is dissolved in 61 ml of warm acetone and treated with a solution of 69.3 g (0.171 mol) of di-p-toluoyl-l-tartaric acid monohydrate in 98 ml acetone. The solution is stirred until homogeneous, allowed to stand 18 hours at 25° C., and then cooled in the freezer to 0° C. for 4 hours. The salt that forms is removed by filtration, washed once with cold acetone, collected, and dried at 60° C. (vacuum oven) to give 68.8 g of D as a white solid, $[\alpha]_{589} = -127.1°$ (abs. EtOH), m.p. 136°-144° C. (foam).

Salt D is dissolved in 2900 ml of boiling acetone, filtered, concentrated to 900 ml, allowed to stand 18 hours at 25° C., and then colled in the freezer to 0° C. for 4 hours. The precipitate is removed by filtration, washed once with cold acetone, collected and dried at 60° C. (vacuum oven) to give 36.5 g of E as a white solid, $[\alpha]_{589} = +132.0°$ (abs. EtOH), m.p. 142°-144° C. (foam).

The resolved salt E (36.5 g, 0.0601 mol) is treated with 300 ml of 10% sodium hydroxide and 300 ml of diethyl ether and the mixture stirred until the solid is dissolved. The ether is separated, dried over MgSO₄, filtered, and evaporated to dryness in vacuo to provide 12.6 g of a tlc (silica GF eluted with 1:9 methanol:chloroform) homogeneous colorless oil. Crystallization from 25 ml of cyclohexane gives 11.26 g of (+)-5-methyl-10,11-dihydro-5H-dibenzo[a,d]cyclohepten-5,10-imine as a white solid, $[\alpha]_{589}{}^{20} = +161.4°$, (C=0.038 g/2 ml ethanol), m.p. 68.5°-69.0° C.

EXAMPLE 15

(+)-5-Methyl-10,11-dihydro-5H-dibenzo[a,d]cyclohepten-5,10-imine hydrogen maleate A solution of 10.05 g (0.0454 mole) of (+)-5-Methyl-10,11-dihydro-5H-dibenzo[a,d]cyclohepten-5,10-imine in 25 ml of absolute ethanol is filtered into a flask and the filter is washed with absolute ethanol to a final filtrate volume of 40 ml. A solution of 5.27 g (0.0454 mole) of maleic acid in 20 ml of absolute ethanol is filtered into the same flask. The combined filtrates are mixed, seeded, held at room temperature for a short time, then refrigerated overnight. The crystalline material is collected and dried to give (+)-5-methyl-10,11-dihydro-5H-dibenzo[a,d]cyclohepten-5,10-imine hydrogen maleate, m.p. 208.5°-210° C.; $[\alpha]_D{}^{20} + 114°$, (C=0.0128 g/2 ml of ethanol).

EXAMPLE 16

2-Methoxy-5-methyl-10,11-dihydro-5H-dibenzo[a,d]cyclohepten-5,10-imine hydrochloride Step A. Preparation of 2-Methoxy-10,11-dihydro-5H-dibenzo[a,d]cyclohepten-5-one A mixture of phthalic anhydride (89.6 g, 0.605 mol), m-methoxyphenylacetic acid, (100.5 g, 0.605 mol), and freshly fused sodium acetate (3.0 g) is heated to 255° C. for 1 hour under a Dean-Stark receiver. The orange melt is poured onto aluminum foil and allowed to cool. The solid residue is recrystallized from absolute ethanol (2500 ml) to give 111.5 g (73%) of (3-methoxybenzal)phthalide as a yellow solid: m.p. 119°-123° C. Without further purification it (111.5 g, 0.441 mol) is hydrogenated with Raney nickel (6 tablespoons) at 25° C. and 40 psi in absolute ethanol (3000 ml). The catalyst is removed by filtration through super cel and the filtrate is evaporated to dryness under reduced pressure. The oily residue is slurried with methylene chloride (1000 ml) and extracted with aqueous saturated NaHCO₃ (3×500 ml). The basic aqueous extracts are combined, warmed on a steam bath to remove excess methylene chloride, filtered, and the filtrate acidified with 6 N hydrochloric acid to give 70.9 g (63%) of 2-[2-(3-methoxyphenyl)-ethyl]benzoic acid as a white solid: m.p. 119°-122° C. Without further purification it (70.9 g, 0.276 mol) is treated with polyphosphoric acid (437 g) and heated to 100° C. After 2 hours, the reaction mixture is hydrolyzed in ice water and the aqueous phase is extracted with ether (3×300 ml). The combined etheral extracts are washed with aqueous saturated NaHCO₃ (1×150 ml), H₂O (2×150 ml), dried over MgSO₄ and filtered, and the filtrate evaporated to dryness under reduced pressure. Treatment of the residue with ether gives 60.6 g (92%) of title compound as a light yellow solid: m.p. 74°–76° C.

Step B. Preparation of 10,11-Dibromo-2-methoxy-10,11-dihydro-5H-dibenzo[a,d]cyclohepten-5-one A mixture of 2-methoxy-10,11-dihydro-5H-dibenzo[a,d]cyclohepten-5-one (53.8 g, 0.226 mol), N-bromosuccinimide (88.4 g, 0.497 mol), and dibenzoyl peroxide (1.0 g) in carbon tetrachloride (1100 ml) is heated under reflux for 1 hour. The cooled mixture is filtered to remove solid succinimide and the filtrate is washed with 5% NaOH (1×150 ml) and H₂O (2×150 ml), dried over MgSO₄ and filtered, and the filtrate evaporated to dryness under reduced pressure. Treatment of the oily residue with ether gives 75.7 g ((85%) of the title compound as a white solid. A sample, recrystalized from ether, has m.p. 138°–139.5° C.

Step C. Preparation of 10(11)-Bromo-2-methoxy-5H-dibenzo[a,d]cyclohepten-5-one

A mixture of 10(11)-dibromo-2-methoxy-10,11-dihydro-5H-dibenzo[a,d]cyclohepten-5-one (37.5 g, 0.0947 mol) and KOH (16.2 g, 0.289 mol) in methanol (275 ml) is heated to reflux for 2 hours. The solvent is evaporated under reduced pressure and the residue is slurried with H₂O (500 ml) and extracted with methylene chloride (3×300 ml). The combined extracts are dried over MgSO₄ and filtered and the filtrate is evaporated to give 29.4 (98%) of title compound as a mixture of isomers. Treatment with ether provides a single isomer with m.p. 112.5°–114.5° C.

Step D. Preparation of 2-Methoxy-10(11)-(4'-methylpiperazin-1-yl)-5H-dibenzo[a,d]cyclohepten-5-one To a solution of 10(11)-bromo-2-methoxy-5H-dibenzo[a,d]cyclohepten-5-one (17.1 g, 0.0543 mol) and N-methyl piperazine (13.3 g, 0.133 mol) in dry dioxane (136 ml) is added potassium tert-butoxide (10.1 g, 0.090 mol). The reaction mixture is stirred and heated under reflux for 1 hour. The solvent is evaporated under reduced pressure and the residue is slurried with H₂O (200 ml) and extracted with chlofoform (3×250 ml). The combined extracts are dried over MgSO₄ and filtered and the filtrate evaporated to dryness to give 20 g of orange oil as a 1:1 mixture of isomers; ¹H nmr (CDCl₃) 2.37 (s, 3H, NCH₃), 2.43–3.12 (m, 8H, NCH₂—), 3.80 and 3.87 (s, 3H, OCH₃), 6.27 and 6.33 (s, 1H, vinyl), 6.70–8.08 (m, 7H, aromatic)/ m/e (%) 334 (25, m+), 86 (21), 71 (15), 70 (100), 43 (25).

Trituration of the orange oil with ether gives a single isomer in which the piperazine moiety is attached to position 10 of the tricyclic ring: m.p. 140°–142° C.

Evaporation of the ether from the above trituration gives a 3:1 mixture of isomers in favor of that isomer in which the piperazine moiety is attached to position 11 of the tricyclic ring.

Step E. Preparation of 2-Methoxy-5-methyl-10-(4'-methylpiperazin-1-yl)-5H-dibenzo[a,d]cyclohepten-5-ol To a solution of methyl lithium in ether (1.84 m, 37.8 ml) diluted with ether (40 ml) is added with stirring a solution of 2-methoxy-10-(4'-methylpiperizin-1-yl)-5H-dibenzo[a,d]cyclohepten-5-one (17.9 g, 0.0535 mol9 in dry THF (80 ml) while the temperature is maintained at 0°–5° C. After 1 hour, tlc (silica gel eluted with 1:9 v/v CH₃OH:CHCl₃) shows the disappearance of starting material. The reaction is poured into ice water (600 ml) and extracted with chloroform (3×250 ml). The chloroform extracts are combined, dried over MgSO₄ and filtered, and the filtrate evaporated to dryness under reduced pressure. Trituration of the residue with acetonitrile gives 13.0 g (69%) of the title compound as a solid. Recrystallization from acetonitrile gives a 2:1 mixture of diastereomers: m.p. 147°–151° C.

Step F. Preparation of 2-Methoxy-5-methylene-10-oxo-10,11-dihydro-5H-dibenzo[a,d]cyclohepten-5-one A solution of 2-methoxy-5-methyl-10-(4'-piperazin-1-yl)-5H-dibenzo[a,d]cyclohepten-5-ol (7.0 g, 0.020 mol) in ethanol (21 ml) is treated with ethanolic HCl (13.6 ml, 8.45 N), hydrochloric acid (2.8 ml, 12 N) and H₂O (5.6 ml). The mixture is stirred at 25° for 1 hour and then heated under reflux for 1 hour. The solvent is concentrated under reduced pressure, and the concentrate is diluted with H₂O (75 ml) and extracted with ether (3×100 ml). The combined extracts are dried over MgSO₄ and filtered, and the filtrate is evaporated. Recrystallization of the residue from ether gives 4.05 g (81%) of title compound m.p. 137°–139° C.

Step G: Preparation of 2-Methoxy-5-methylene-10-hydroximino-10,11-dihydro-5H-dibenzo[a,d]cycloheptene A solution of 2-methoxy-5-methylene-10-oxo-10,11-dihydro-5H-dibenzo[a,d]cycloheptene (9.7 g, 0.0388 mol), hydroxylamine hydrochloride (3.42 g, 0.0492 mol), and sodium acetate (4.26 g, 0.0519 mol) in methanol (194 ml) is heated under reflux for 2 hours. The solvent is removed under reduced pressure, the residue is slurried in water (200 ml), the pH is adjusted to 8 with concentrated aqueous ammonia, and the slurry is extracted with ether (3×105 ml). The combined extracts are dried over MgSO₄ and filtered, and the filtrate is evaporated to yield 10.1 g (98%) of crude material. A sample recrystallized from ether has m.p. 125°–127° C.

Step H. Preparation of 2-Methoxy-5-methylene-10-hydroxamino-10,11-dihydro-5H-dibenzo[a,d]cycloheptene To a solution of 2-methoxy-5-methylene-10-hydroximino-10,11-dihydro-5H-dibenzo[a,d]cycloheptene (8.74 g, 0.0329 mol) in methanol (191 ml) is added sodium cyanoborohydride (5.9 g) in one portion followed by 12 N hydrochloric acid in methanol [1:1 (v/v)] added dropwise to maintain the pH at the turning point of methyl orange indicator. After 3 hours, tlc (silica developed with CHCl₃) indicates disappearance of starting material (R$_f$0.22) and formation of product (R$_f$ 0.09). The solvent is removed under reduced pressure and the residue is slurried with water (100 ml). The pH is adjusted to 8.5 with concentrated aqueous ammonia, and the mixture is extracted with ether (3×120 ml). The combined extracts are dried over MgSO₄, and filtered, and the filtrate is evaporated to dryness. The crystalline residue is triturated with ether to yield 6.9 g (78%) of title compound; m.p. 120°–122° C.

Step I. Preparation of 12-Hydroxy-2-methoxy-5-methyl-10,11-dihydro-5H-dibenzo[a,d]cyclohepten-5,10-imine A suspension of 2-methoxy-5-methylene-10-hydroxamino-10,11-dihydro-5H-dibenzo[a,d]cycloheptene (5.96 g, 0.0223 mol) in octane (655 ml) is refluxed for 2 hours. The solvent is removed under reduced pressure and the oily residue crystallized with diethyl ether to give 3.58 g (60%) of product as a 3:2 mixture of isomers: m.p. 197°–200.5° C.

Step J. Preparation of 2-Methoxy-5-methyl-10,11-dihydro-5H-dibenzo[a,d]cyclohepten-5,10-imine hydrochloride To a solution of 12-hydroxy-2-methoxy-5-methyl-10,11-dihydro-5H-dibenzo[a,d]cyclohepten-5,10-imine (5.27 g, 0.0197 mol), in glacial acetic acid (105 ml) is added portionwise, zinc dust (4.9 g). The mixture is stirred and heated at 65° C. for 2 hours. The mixture is filtered through a pad of celite and the filtrate is slurried with ice (100 g). The pH is adjusted to 8.5 with concentrated aqueous ammonia, and the mixture is extracted with ether (3 × 100 ml). The combined extracts are dried over $MgSO_4$ and filtered, and the filtrate is evaporated to dryness to give 4.86 g (98%) of a yellow oil. The oil is dissolved in ethanolic hydrogen chloride and the solution is evaporated to dryness. The residue is recrystallized from ethanol to yield the title compound as an ethanol solvate m.p. 250° C.

EXAMPLE 17

2-Hydroxy-5-methyl-10,11-dihydro-5H-dibenzo[a,d]cyclohepten-5,10-imine

A mixture of 2-methoxy-5-methyl-10,11-dihydro-5H-dibenzo[a,d]cyclohepten-5,10-imine (2.7 g, 0.0107 mol) and pyridinium hydrochloride (16.2 g) is stirred at 200° for 2 hours. The melt is cooled to 50° C. and slurried with water (75 ml). The slurry is made basic with aqueous saturated $NaHCO_3$ and extracted with ether (3 × 100 ml). The combined extracts are dried over $MgSO_4$ and filtered, and the filtrate evaporated to dryness under reduced pressure to give 2.19 g of crude product. Column chromatography (silica gel with 2% methanol in chloroform) provides a solid which is recrystallized from ethyl acetate to give 1.20 g (47%) of pure title compound; m.p. 215°–217° C.

EXAMPLE 18

8-Methoxy-5-methyl-10,11-dihydro-5H-dibenzo[a,d]cyclohepten-5,10-imine hydrochloride Step A. Preparation of 2-Methoxy-5-methylene-11-oxo-10,11-dihydro-5H-dibenzo[a,d]cycloheptene To a solution of methyl lithium in ether (1.84 M, 38.4 ml) diluted with ether (41 ml) is added with stirring a solution of a ⅓ mixture of 2-methoxy-10(11)-(4'-methylpiperazin-1-yl)-5H-dibenzo[a,d]cyclohepten-5-one (Example 16, Step D) (18.2 g, 0.0544 mol) in dry THF (80 ml) while the temperature is maintained at 0°–5° C. After 1 hour, tlc (silica gel eluted with 1:9 v/v $CH_3OH:CHCl_3$) shows the disappearance of material. The reaction is poured into ice water (600 ml) and extracted with chloroform (3 × 250 ml). The chloroform extracts are combined, dried over $MgSO_4$ and filtered, and the filtrate evaporated to dryness under reduced pressure to give 19.0 g of crude 5-methyl carbinol as a solid. The solid is dissolved in ethanol (58 ml), and ethanolic HCl (37 ml, 8.45 N), hydrochloric acid (7.6 ml, 12 N), and water (15.2 ml) are added. The mixture is stirred at 25° C. for 1 hour and then heated under reflux for 2 hours. The solvent is concentrated under reduced pressure, and the concentrate is diluted with water (200 ml) and extracted with ether (3 × 200 ml). The combined extracts are dried over $MgSO_4$ and filtered, and the filtrate is evaporated to give 13.0 g of a ⅓ mixture of 10(11)-oxo compound as a crude brown oil. Chromatography of the mixture on silica gel (1000 g, $CHCl_3$ elution) separated 11-oxo compound (7.8 g, $R_f$ 0.67) from 10-oxo compound (1.7 g, $R_f$ 0.58). Recrystallization of a sample of 11-oxo compound from ether gives the product with m.p. 97°–99.5° C.

Step B. Preparation of 2-Methoxy-5-methylene-11-hydroximino-10,11-dihydro-5H-dibenzo[a,d]cycloheptene A solution of 2-methoxy-5-methylene-11-oxo-10,11-dihydro-5H-dibenzo[a,d]cycloheptene (9.0 g, 0.0360 mol), hydroxylamine hydrochloride (3.17 g, 0.0457 mol), and sodium acetate (3.95 g, 0.0482 mol) in methanol (180 ml) is heated under reflux for 2.5 hours. The solvent is removed under reduced pressure, the residue is slurried in water (190 ml), the pH is adjusted to 8 with concentrated aqueous ammonia, and the slurry is extracted with ether (3 × 140 ml). The combined extracts are dried over $MgSO_4$ and filtered and the filtrate is evaporated to yield 8.37 g (87%) of crude material. A sample recrystallized from ether has m.p. 128°–131° C.

Step C. Preparation of 2-Methoxy-5-methylene-11-hydroxamino-10,11-dihydro-5H-dibenzo[a,d]cycloheptene To a solution of 2-methoxy-5-methylene-11-hydroximino-10,11-dihydro-5H-dibenzo[a,d]cycloheptene (7.87 g, 0.0297 mol) in methanol (173 ml) is added sodium cyanoborohydride (6.0 g) in one portion followed by 12 N hydrochloric acid in methanol [1:1 (v/v)] added dropwise to maintain the pH at the turning point of methyl orange indicator. After 3 hours, tlc (silica eluted with $CHCl_3$) shows disappearance of starting material ($R_f$ 0.25) and formation of product ($R_f$ 0.10). The solvent is removed under reduced pressure and the residue is slurried with water (100 ml). The pH is adjusted to 8.5 with concentrated aqueous ammonia, and the mixture is extracted with ether (3 × 125 ml). The combined extracts are dried over $MgSO_4$ and filtered, and the filtrate is evaporated to dryness to yield 7.90 g (99%) of crude title compound. A sample recrystallized from ether has m.p. 119°–121.5° C.

Step D. Preparation of 12-Hydroxy-8-methoxy-5-methyl-10,11-dihydro-5H-dibenzo[a,d]cyclohepten-5,10-imine A suspension of 2-methoxy-5-methylene-11-hydroxamino-10,11-dihydro-5H-dibenzo[a,d]cycloheptene (6.0 g, 0.0224 mol) in octane (655 ml) is refluxed over 2 hours. The reaction is cooled and the solvent removed under reduced pressure. Crystallization of the oily residue with diethyl ether gives 3.35 g (56%) of title compound as a colorless solid homogeneous to tlc (silica GF in 2% $MeOH/98\%$ $CH_2Cl_2$), m.p. 158.0°–159.5° C.

Step E. Preparation of 8-Methoxy-5-methyl-10,11-dihydro-5H-dibenzo[a,d]cyclohepten-5,10-imine hydrochloride To a solution of 12-hydroxy-8-methoxy-5-methyl-10,11-dihydro-5H-dibenzo[a,d]cyclohepten-5,10-imine (5.0 g, 0.0187 mol) in glacial acetic acid (100 ml) is added portionwise zinc dust (4.7 g). The mixture is stirred, heated at 65° C. for 1 hour, and filtered through a pad of celite. The filtrate is treated with 100 g of ice, basified with conc. ammonium hydroxide, and extracted with ether (3 × 100 ml). The combined ethereal extracts are dried over $MgSO_4$ and filtered, and the filtrate is concentrated under reduced pressure. The resulting yellow oil (4.67 g, 99% crude yield) is dissolved in 35 ml of absolute ethanol and treated with ethanolic hydrogen chloride. Filtration of the precipitate provides 3.7 g of a white solid, which after recrystallization from 70 ml ethanol, gives 1.7 g of title compound as a white solid homogenous to tlc (silica GF in butanol/acetic acid/water at 5/3/2): m.p. 305.5°–306.5° C.

EXAMPLE 19

8-Hydroxy-5-methyl-10,11-dihydro-5H-dibenzo[a,d]cyclohepten-5,10 imine

A mixture of 8-methoxy-5-methyl-10,11-dihydro-5H-dibenzo[a,d]cyclohepten-5,10-imine (1.75 g, 0.00696 mol) and pyridinium hydrochloride (10.5 g) is stirred at 190° for 2.5 hr. The melt is cooled to 50° C. and slurried with water (50 ml). The slurry is made basic with aqueous saturated NaHCO$_3$ and extracted with ethyl acetate (3×50 ml). The combined extracts are dried over MgSO$_4$ and filtered and the filtrate evaporated to dryness under reduced pressure to give 1.62 g (98%) of crude title compound. A sample recrystallized from ethyl acetate has m.p. 245°–247° C.

EXAMPLE 20

(+)-12-Cyclopropylmethyl-5-methyl-10,11-dihydro-5H-dibenzo[a,d]cyclohepten-5,10-imine hydrochloride Step A. Preparation of (+)-12-cyclopropylcarbonyl-5-methyl-10,11-dihydro-5H-dibenzo[a,d]cyclohepten-5,10-imine A suspension of 6.0 g (0.178 mol) of (+)-5-methyl-10,11-dihydro-5H-dibenzo[a,d]cyclohepten-5,10-imine hydrogen maleate in 60 ml of water and 120 ml of ether is treated with 18 ml of 1 N sodium hydroxide solution. The mixture is cooled in an ice bath and treated with another 18 ml of 1 N sodium hydroxide followed by the dropwise addition of a solution of 1.62 g of cyclopropane carboxylic acid chloride with vigorous stirring. After the addition is complete the reaction mixture is stirred 1 hour at 0° C. Ether (60 ml) is added to dissolve a precipitate. With continued cooling in an ice bath an additional 6 ml of 1 N sodium hydroxide followed by 0.3 ml of cyclopropane carboxylic acid chloride in 3 ml of ether are added and stirring is continued another 20 min.

The aqueous phase is separated and extracted twice with ether. The combined extracts and original ether phase are washed twice with water, dried over MgSO$_4$, filtered and concentrated to near dryness in vacuo to give a solid (4.5 g), m.p. 154°–157° C. An additional 0.5 g is obtained from the mother liquors.

Step B. Preparation of (+)-12-cyclopropylmethyl-5-methyl-10,11-dihydro-5H-dibenzo[a,d]cyclohepten-5,10-imine hydrochloride A 250 ml 3-neck, round-bottom flask fitted with a magnetic stirrer, septum, condenser and a nitrogen inlet is charged with 4.0 g (0.0138 mol) of amide from Step A in 24 ml of tetrahydrofuran (THF). With ice-bath cooling, 23.1 ml of borane (BH$_3$) in THF (1 M) is added over about 5 minutes with stirring. The ice bath is removed and stirring is continued for 75 mins at 75° C. After cooling in an ice-bath, water is added slowly until gas evolution ceases. The mixture is concentrated to dryness in vacuo. The residue is partitioned between water and ether, the aqueous phase is separated, extracted twice with ether and the combined ether extracts and original ether phases are washed with saturated sodium chloride solution and water and dried over MgSO$_4$, filtered and concentrated to dryness in vacuo to give 4.1 g crude product.

The crude product is combined with that of a previous experiment to give 5.0 g which is chromatographed on 300 g of silica gel packed in 4% (v/v) methanol in methylene chloride. The crude product is applied to the column as a methylene chloride solution and is eluted with 4% (v/v) methanol in methylene chloride, collecting 21×100 ml fractions. The fractions are combined and concentrated to dryness as follows:

| Fraction | TLC | WT | COMMENT |
| --- | --- | --- | --- |
| 1 + 2 | NIL | — | Discard |
| 3 | upper component | 2.0 g | Foam (I) |
| 4 | upper component & product | 2.0 g | Foam (II) |
| 5 – 21 | product | 1.37 g | Oil (III) |

Compounds I and II are combined in acetone solution, cooled in ice and treated with gaseous hydrogen chloride for 10 min. and stirred one hour. The solution is concentrated to dryness in vacuo. The residue is partitioned between water and ether and basified by the addition of aqueous sodium hydroxide solution. The aqueous phase is separated and extracted with ether and the combined ether extracts and original ether phase are washed with water, dried over MgSO$_4$, filtered and concentrated to dryness in vacuo to give an oil (3.5 g). The oil is chromatographed on 200 g of silica gel by elution with methylene chloride until the first component is eluted (0.52 g). Elution is continued with 3% (v/v) methanol in methylene chloride and the combined product fractions (3.0 g) are combined with fraction (III) from the first chromatographic separation. The material is dissolved in ether, filtered and concentrated to dryness in vacuo to give 3.6 g, m.p. 88°–92° C. Conversion to the hydrochloride salt gives material with m.p. 242°–244° C., $[\alpha]_D^{25}$ +147.7° (c, 0.0104 g/ml ethanol).

Using the procedure substantially as described in Example 20, but substituting for the cyclopropane carboxylic acid chloride used therein, an equimolar amount of acetyl chloride and propionyl chloride there are produced respectively: (+)-12-ethyl-5-methyl-10,11-dihydro-5H-dibenzo[a,d]cyclohepten-5,10-imine hydrochloride, m.p. 275°–276° C., $[\alpha]_D^{25}$ +163.5° (C, 0.01845 g/ml ethanol); and (+)-5-methyl-12-propyl-10,11-dihydro-5H-dibenzo[a,d]cyclohepten-5,10-imine hydrochloride, m.p. 255°–256° C., $[\alpha]_D^{25}$ +160.2° (C, 0.0124 g/ml ethanol).

EXAMPLE 21

12-(2-Dimethylaminoethyl)-5-methyl-10,11-dihydro-5H-dibenzo[a,d]cyclohepten-5-10-imine hydrogen fumarate 5-Methyl-10,11-dihydro-5H-dibenzo[a,d]cyclohepten-5,10-imine (1.5 g, 6.8 mmole) and 1-chloro-2-(dimethylamino)ethane (1.1 g, 10.2 mmole) are combined in hexamethylphosphoric triamide (2 ml) and heated at 120° for 4 hr. The mixture is cooled and chromatographed on silica gel (650 ml, 4 cm diameter column) by elution with 5% methanol in chloroform. The product fractions are evaporated in vacuo, and the residue (850 mg) is dissolved in ethyl acetate (25 ml) and combined with a solution of fumaric acid (350 mg) in methanol (10 ml). The resulting mixture is filtered and evaporated in vacuo, and the residue is dissolved in acetone (20 ml) and refrigerated. The title compound (700 mg) is collected by filtration; m.p. 193°–196° C.

EXAMPLE 22

Preparation of intravenous solutions

A solution containing 10 mg of (+)-5-methyl-10,11-dihydro-5H-dibenzo[a,d]cyclohepten-5,10-imine hydrogen maleate per ml of injectable solution is prepared in the following manner.

A mixture of 10 mg of active ingredient and 9 mg of sodium chloride is dissolved in sufficient water for injection to make 1 ml of solution. The pH is adjusted using hydrochloric acid or aqueous sodium hydroxide to about pH 7.0.

If it is desired that the intravenous solution be used for multi-dose purposes, 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg, respectively, of active ingredient per ml of solution are similarly prepared substituting the indicated amount for the above-illustrated 10 mg quantity. Bulk injectable solutions of convenient volume for subsequent delivery in unit dosage form are readily prepared following the above procedure.

Following the above procedure, other representative injectable solutions of the present invention are prepared when (+)-5-methyl-10,11-dihydro-5H-dibenzo[a,d]cyclohepten-5,10-imine hydrogen maleate is replaced by an equivalent amount of any of the novel compounds of the present invention.

EXAMPLE 23

Tablet Preparation

Tablets containing 1.0, 2.0, 25.0, 26.0, 50.0 and 100.0 mg, respectively, of (+)-5-methyl-10,11-dihydro-5H-dibenzo[a,d]cyclohepten-5,10-imine hydrogen maleate are prepared as illustrated below.

| TABLE FOR DOSES CONTAINING FROM 1–25 MG OF THE ACTIVE COMPOUND | | | |
|---|---|---|---|
| | Amount - mg | | |
| (+)-5-methyl-10,11-dihydro-5H-dibenzo[a,d]cyclohepten-5,10-imine hydrogen maleate | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–200 MG OF THE ACTIVE COMPOUND | | | |
|---|---|---|---|
| | Amount - mg | | |
| (+)-5-methyl-10,11-dihydro-5H-dibenzo[a,d]cyclohepten-5,10-imine hydrogen maleate | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet. Other tablets are prepared using the same procedures and the equivalent amounts of excipients along with equivalent amounts of any of the novel compounds of the present invention.

What is claimed is:

1. A compound of the structural formula

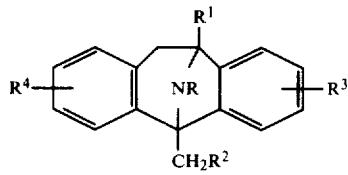

or a pharmaceutically acceptable salt thereof wherein:
R is
  (1) hydrogen,
  (2) $C_{1-5}$ alkyl,
  (3) $C_{2-5}$ alkenyl,
  (4) phenyl-$C_{1-3}$ alkyl,
  (5) halophenyl-$C_{1-3}$ alkyl,
  (6) $C_{1-3}$ alkylphenyl-$C_{1-3}$ alkyl,
  (7) $C_{3-6}$ cycloalkyl,
  (8) $C_{3-6}$ cycloalkyl-$C_{1-3}$ alkyl,
  (9) di($C_{1-3}$ alkyl)amino-$C_{1-3}$ alkyl; or
  (10) hydroxy;
$R^1$ is
  (1) hydrogen,
  (2) $C_{1-5}$ alkyl,
  (3) $C_{2-5}$ alkenyl,
  (4) phenyl-$C_{1-3}$ alkyl,
  (5) $C_{3-6}$ cycloalkyl
  (6) $C_{3-6}$ cycloalkyl-$C_{1-3}$ alkyl;
—$CH_2R^2$ is
  (1) methyl,
  (2) ethyl or
  (3) hydroxyethyl; and
$R^3$ and $R^4$ are independently
  (1) hydrogen,
  (2) halogen,
  (3) $C_{1-5}$ alkoxy,
  (4) trifluoromethylthio,
  (5) cyano,
  (6) carboxy, or
  (7) hydroxy.

2. The compound of claim 1 wherein $R^1$ is hydrogen.

3. The compound of claim 1 wherein $R^1$, $R^3$ and $R^4$ are hydrogen; R is hydrogen, $C_{1-5}$ alkyl, $C_{2-5}$ alkenyl or $C_{3-6}$ cycloalkyl-$C_{1-3}$ alkyl; and —$CH_2R^2$ is methyl or ethyl.

4. The compound of claim 3 wherein $R^1$, $R^3$ and $R^4$ are hydrogen, R is hydrogen, or $C_{1-5}$ alkyl; and —$CH_2R^2$ is methyl or ethyl.

5. The compound of claim 4 which is racemic 5-methyl-10,11-dihydro-5H-dibenzo[a,d]cyclohepten-5,10-imine, its optically active isomers, or a pharmaceutically acceptable salt thereof.

6. The compound of claim 4 which is (+)-5-methyl-10,11-dihydro-5H-dibenzo[a,d]cyclohepten-5,10-imine or a pharmaceutically acceptable salt thereof.

7. A pharmaceutical composition useful as an anticonvulsant, comprising a pharmaceutical carrier and an effective anticonvulsant amount of a compound of structural formula:

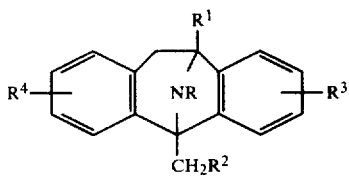

or a pharmaceutically acceptable salt thereof wherein:
R is
  (1) hydrogen,
  (2) $C_{1-5}$ alkyl,
  (3) $C_{2-5}$ alkenyl,
  (4) phenyl-$C_{1-3}$ alkyl,
  (5) halophenyl-$C_{1-3}$ alkyl,
  (6) $C_{1-3}$ alkylphenyl-$C_{1-3}$ alkyl,
  (7) $C_{3-6}$ cycloalkyl,
  (8) $C_{3-6}$ cycloalkyl-$C_{1-3}$ alkyl,
  (9) di($C_{1-3}$ alkyl)amino-$C_{1-3}$ alkyl; or
  (10) hydroxy;
$R^1$ is
  (1) hydrogen,
  (2) $C_{1-5}$ alkyl,
  (3) $C_{2-5}$ alkenyl,
  (4) phenyl-$C_{1-3}$ alkyl,
  (5) $C_{3-6}$ cycloalkyl,
  (6) $C_{3-6}$ cycloalkyl-$C_{1-3}$ alkyl;
—$CH_2R^2$ is
  (1) methyl
  (2) ethyl or
  (3) hydroxyethyl; and
$R^3$ and $R^4$ are independently
  (1) hydrogen,
  (2) halogen,
  (3) $C_{1-5}$ alkoxy,
  (4) trifluoromethylthio,
  (5) cyano,
  (6) carboxy, or
  (7) hydroxy.

8. The composition of claim 7 wherein $R^1$ is hydrogen.

9. The composition of claim 7 wherein $R^1$, $R^3$ and $R^4$ are hydrogen; R is hydrogen, $C_{1-5}$ alkyl, $C_{2-5}$ alkenyl or $C_{3-6}$ cycloalkyl-$C_{1-3}$ alkyl; and —$CH_2R^2$ is methyl or ethyl.

10. The composition of claim 9 wherein $R^1$, $R^3$ and $R^4$ are hydrogen; R is hydrogen, or $C_{1-5}$ alkyl; and —$CH_2R^2$ is methyl or ethyl.

11. The pharmaceutical composition of claim 10 wherein the compound is racemic 5-methyl-10,11-dihydro-5H-dibenzo[a,d]cyclohepten-5,10-imine, its optically active isomers, or a pharmaceutically acceptable salt thereof.

12. The pharmaceutical composition of claim 10 wherein the compound is (+)-5-methyl-10,11-dihydro-5H-dibenzo[a,d]cyclohepten-5,10-imine or a pharmaceutically acceptable salt thereof.

13. A method of treating convulsions, comprising administering to a patient in need of such treatment an effective anticonvulsant amount of a compound of structural formula:

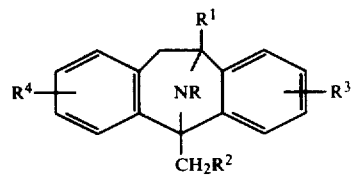

or a pharmaceutical acceptable salt thereof wherein:
R is
  (1) hydrogen,
  (2) $C_{1-5}$ alkyl,
  (3) $C_{2-5}$ alkenyl,
  (4) phenyl-$C_{1-3}$ alkyl,
  (5) halophenyl-$C_{1-3}$ alkyl,
  (6) $C_{1-3}$ alkylphenyl-$C_{1-3}$ alkyl,
  (7) $C_{3-6}$ cycloalkyl,
  (8) $C_{3-6}$ cycloalkyl-$C_{1-3}$ alkyl,
  (9) di($C_{1-3}$ alkyl)amino-$C_{1-3}$ alkyl; or
  (10) hydroxy;
$R^1$ is
  (1) hydrogen,
  (2) $C_{1-5}$ alkyl
  (3) $C_{2-5}$ alkenyl,
  (4) phenyl-$C_{1-3}$ alkyl,
  (5) $C_{3-6}$ cycloalkyl,
  (6) $C_{3-6}$ cycloalkyl-$C_{1-3}$ alkyl;
—$CH_2R^2$ is
  (1) methyl,
  (2) ethyl or
  (3) hydroxyethyl; and
$R^3$ and $R^4$ are independently
  (1) hydrogen,
  (2) halogen,
  (3) $C_{1-5}$ alkoxy,
  (4) trifluoromethylthio,
  (5) cyano,
  (6) carboxy, or
  (7) hydroxy.

14. The method of claim 13 wherein $R^1$ is hydrogen.

15. The method of claim 14 wherein $R^1$, $R^3$ and $R^4$ are hydrogen; R is hydrogen, $C_{1-5}$ alkyl, $C_{2-5}$ alkenyl or $C_{3-6}$ cycloalkyl-$C_{1-3}$ alkyl; and —$CH_2R^2$ is methyl or ethyl.

16. The method of claim 15 wherein $R^1$, $R^3$ and $R^4$ are hydrogen; R is hydrogen, or $C_{1-5}$ alkyl; and —$CH_2R^2$ is methyl or ethyl.

17. The method of claim 16 wherein the compound is racemic 5-methyl-10,11-dihydro-5H-dibenzo[a,d]cyclohepten-5,10-imine, its optically active isomers, or a pharmaceutically acceptable salt thereof.

18. The method of claim 16, wherein the compound is (+)-5-methyl-10,11-dihydro-5H-dibenzo[a,d]cyclohepten-5,10-imine or a pharmaceutically acceptable salt thereof.

* * * * *